United States Patent
Ho et al.

(10) Patent No.: US 9,248,250 B2
(45) Date of Patent: *Feb. 2, 2016

(54) PATIENT INTERFACE DEVICE WITH LIMITED SUPPORT AREA ON THE FACE

(71) Applicant: RIC INVESTMENTS, LLC, Wilmington, DE (US)

(72) Inventors: Peter Chi Fai Ho, Pittsburgh, PA (US); Jerome Matula, Jr., Apollo, PA (US); Derrick Blake Andrews, Markleton, PA (US); Richard Andrew Sofranko, Finleyville, PA (US); Dana Marie Horn, Lower Burrell, PA (US)

(73) Assignee: RIC INVESTMENTS, LLC, Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 14/224,691

(22) Filed: Mar. 25, 2014

(65) Prior Publication Data

US 2014/0202466 A1 Jul. 24, 2014

Related U.S. Application Data

(63) Continuation of application No. 11/799,802, filed on May 3, 2007, now Pat. No. 8,701,667.

(60) Provisional application No. 60/798,454, filed on May 5, 2006.

(51) Int. Cl.
*A61M 16/06* (2006.01)
*A61M 16/08* (2006.01)

(52) U.S. Cl.
CPC .......... *A61M 16/0605* (2014.02); *A61M 16/06* (2013.01); *A61M 16/0666* (2013.01); *A61M 16/0683* (2013.01); *A61M 16/0816* (2013.01); *A61M 2210/0618* (2013.01)

(58) Field of Classification Search
CPC . A61M 16/00; A61M 16/06; A61M 16/0605; A61M 16/0666; A61M 16/0672; A61M 16/0683; A61M 2016/0661; A62B 18/00; A62B 18/02
USPC ............ 128/207.18, 207.13, 207.11, 200.24, 128/201.22, 201.23, 201.19, 203.12, 128/203.29, 204.18, 205.25, 206.21, 128/206.23–28, 206.18, 206.11
See application file for complete search history.

(56) References Cited

U.S. PATENT DOCUMENTS

| | | |
|---|---|---|
| 4,422,456 A | 12/1983 | Tiep |
| 4,782,832 A | 11/1988 | Trimble |
| 4,915,105 A | 4/1990 | Lee |
| 5,509,409 A | 4/1996 | Weatherholt |
| 5,647,357 A | 7/1997 | Barnett |
| 5,682,881 A | 11/1997 | Winthrop |
| 5,742,965 A | 4/1998 | Leask |
| 5,884,624 A | 3/1999 | Barnett |
| 6,019,101 A | 2/2000 | Cotner |

(Continued)

*Primary Examiner* — Justine Yu
*Assistant Examiner* — Colin W Stuart
(74) *Attorney, Agent, or Firm* — Michael W. Haas

(57) ABSTRACT

A patient interface device includes a support member, a sealing assembly attached to the support member, and a pair of contacting members. The contacting members are coupled to the support member on each side of the sealing assembly. The contacting members are each configured and arranged to contact the user over a limited contacting region, which corresponds to a junction of the orbicularis oris facial muscle, the zygomaticus facial muscle, and the risorius facial muscle.

12 Claims, 33 Drawing Sheets

(56) References Cited

U.S. PATENT DOCUMENTS

| | | | |
|---|---|---|---|
| 6,119,694 A | 9/2000 | Correa | |
| 6,397,874 B1 | 6/2002 | Featheringill | |
| 6,478,026 B1 | 11/2002 | Wood | |
| 6,807,967 B2 | 10/2004 | Wood | |
| 6,895,965 B2 | 5/2005 | Scarberry | |
| 8,127,764 B2 | 3/2012 | Ho | |
| 8,701,667 B1 * | 4/2014 | Ho et al. | 128/206.24 |
| 2003/0005931 A1 | 1/2003 | Jaffre | |
| 2004/0025883 A1 | 2/2004 | Eaton | |
| 2004/0045551 A1 | 3/2004 | Eaton | |
| 2004/0226566 A1 | 11/2004 | Gunaratnam | |
| 2005/0028822 A1 | 2/2005 | Sleeper | |
| 2005/0072428 A1 | 4/2005 | Ho | |
| 2005/0199242 A1 | 9/2005 | Matula, Jr. | |
| 2005/0205096 A1 | 9/2005 | Matula, Jr. | |
| 2005/0241644 A1 | 11/2005 | Gunaratnam | |
| 2006/0060200 A1 * | 3/2006 | Ho et al. | 128/206.24 |
| 2006/0107958 A1 | 5/2006 | Sleeper | |
| 2006/0130844 A1 | 6/2006 | Ho | |
| 2006/0137690 A1 | 6/2006 | Gunaratnam | |
| 2006/0207597 A1 | 9/2006 | Wright | |
| 2006/0231103 A1 | 10/2006 | Matula, Jr. | |
| 2007/0221227 A1 | 9/2007 | Ho | |

* cited by examiner

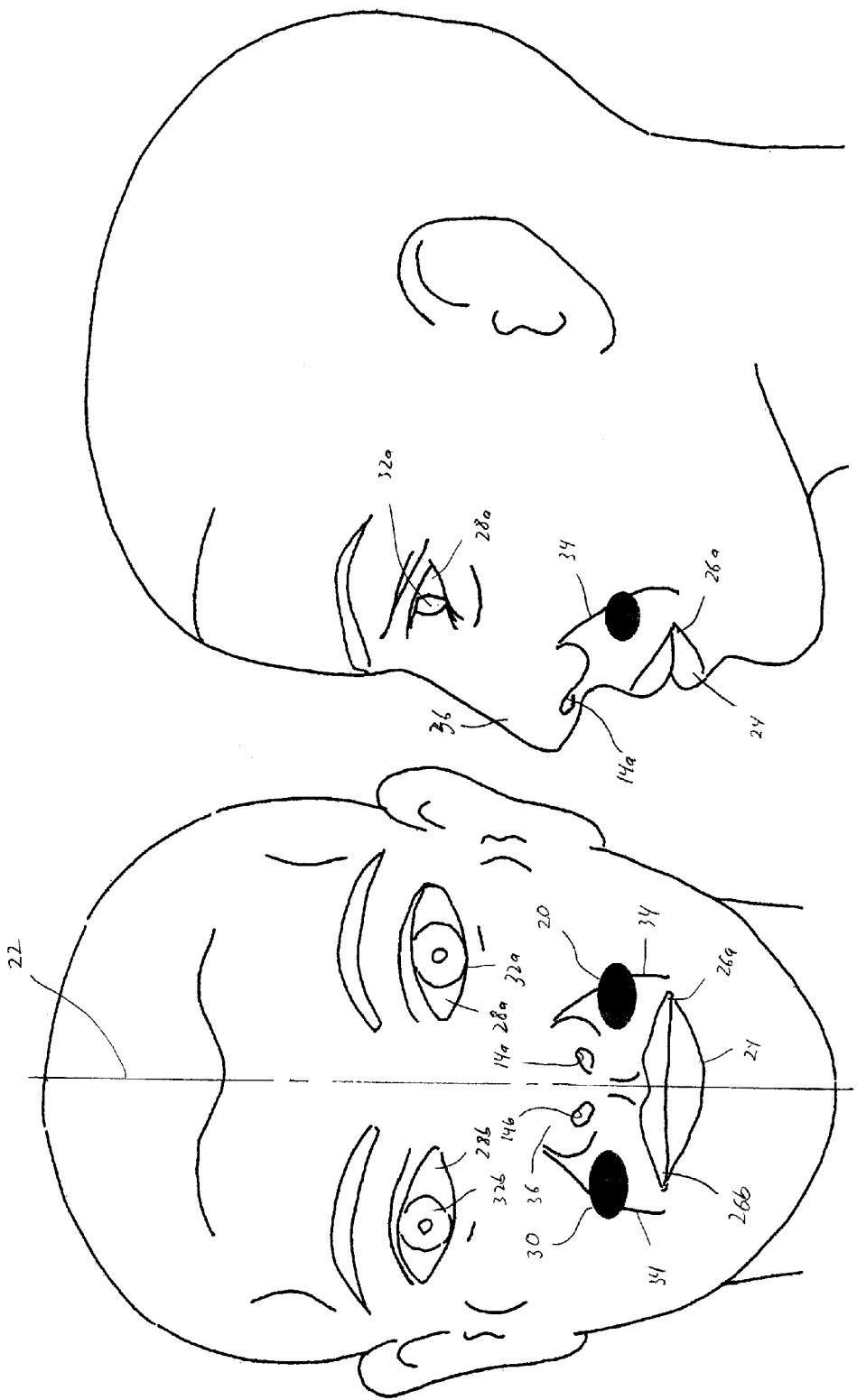

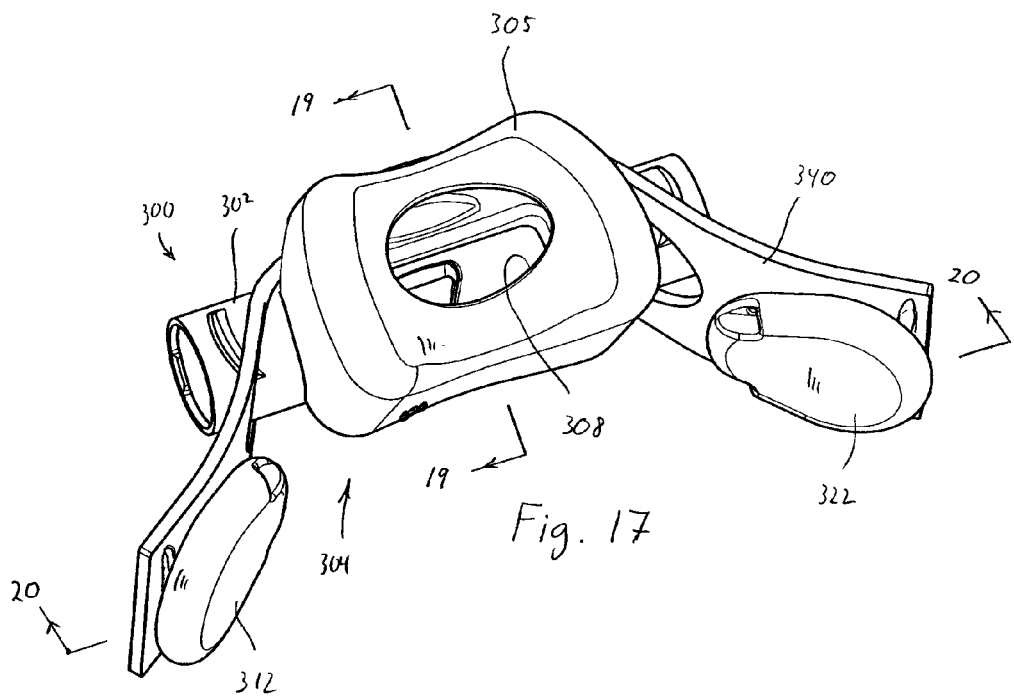
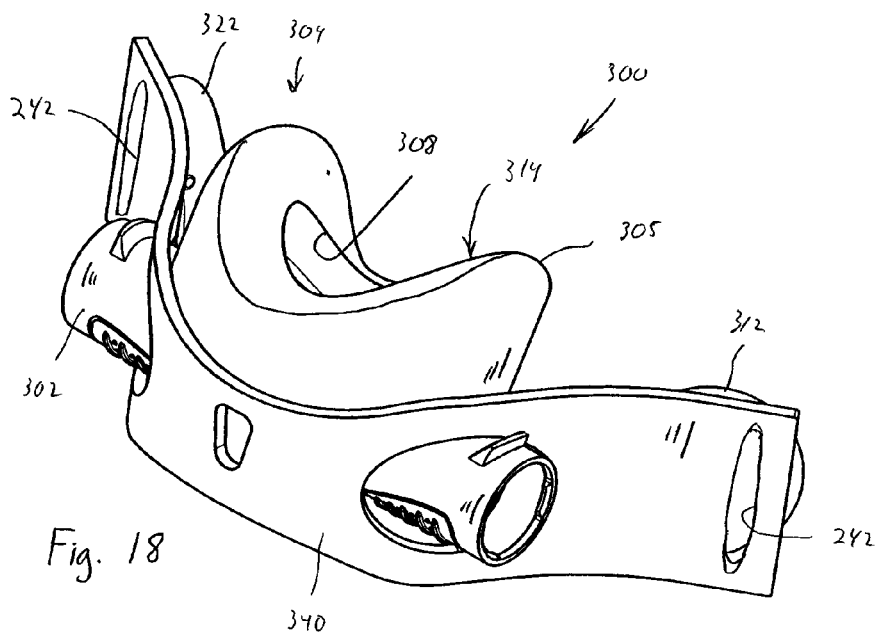

PATIENT INTERFACE DEVICE WITH LIMITED SUPPORT AREA ON THE FACE

CROSS-REFERENCE TO RELATED APPLICATIONS

This application is a Continuation under 35 U.S.C. §120 of U.S. patent application Ser. No. 11/799,802, filed May 3, 2007, which claims priority under 35 U.S.C. §119(e) from provisional U.S. patent application No. 60/798,454, filed May 5, 2006, the contents of which are incorporated herein by reference.

BACKGROUND OF THE INVENTION

1. Field of the Invention

The present invention pertains to a patient interface device that provides a stable platform supporting a sealing assembly that couples a flow of gas with an airway of a patient, is relatively small to minimize the amount of material supported on the patient's face and head, and yet provides a high degree of adjustability, so that the patient interface device fits comfortably on a wide variety of differently sized and shaped patients.

2. Description of the Related Art

There are numerous situations where it is necessary or desirable to deliver a flow of breathing gas non-invasively to the airway of a patient, i.e., without intubating the patient or surgically inserting a tracheal tube in the esophagus. For example, it is known to ventilate a patient using a technique known as non-invasive ventilation. It is also known to deliver continuous positive airway pressure (CPAP) or variable airway pressure, such as a bi-level pressure that varies with the patient's respiratory cycle, or an auto-titrating pressure that varies with the monitored condition of the patient. Typical pressure support therapies are provided to treat a medical disorder, such as sleep apnea syndrome, in particular, obstructive sleep apnea (OSA), or congestive heart failure.

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient. It is known to maintain such masks on the face of a patient by a headgear assembly, which typically have upper and lower straps that wrap around the user's head, where each strap has opposite ends threaded through connecting elements provided on the opposite sides and/or top of a mask.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the interface device provides a tight enough seal against a patient's face without discomfort. A problem arises in that in order for the mask to maintain a seal without any undue gas leaks around the periphery of the mask, the mask cushion may be compressed against the patient's face. This is most notable, for example, in masks having a bubble type cushion. While the bubble cushion itself is comfortable, it does not provide adequate support, which may cause gas leaks around the periphery of the mask. The bubble effect is diminished when the headgear strap force is increased to improve stability.

Some conventional respiratory masks attempt to enhance mask stability by providing a relatively large structure that must be mounted on the patient's face. Therefore, an advantage exists for a respiratory mask that minimizes the amount of material that must be supported on the patient's head and face, yet provides a relatively high degree of stability, so that that the mask is not easily dislodged from the patient. Another advantage exists for a respiratory mask that provides the headgear strapping force needed to hold the mask on the patient to locations on the patient's face that are best suited to handle such forces.

A further advantage exists for a respiratory mask that avoids providing any structural features near the patient's eyes. This advantage is particularly important for patient's who desire to where glasses while wearing the mask and for patient's that tend to feel claustrophobic when a structure is provided at or near their eyes. Avoiding the ocular area also eliminates or avoids the leakage of gas into the user's eyes, which can cause great discomfort. A still further advantage exists for a mask that accomplishes these functions while also providing a relatively high degree of adjustability, so that a common mask style or configuration can be fitted to a variety of differently sized and shaped patients.

SUMMARY OF THE INVENTION

Accordingly, it is an object of the present invention to provide a patient interface device that overcomes the shortcomings of conventional patient interface assemblies. This object is achieved according to one embodiment of the present invention by providing a patient interface device that includes a support member and a sealing assembly attached to the support member. The sealing assembly contacts the user and communicates a flow of gas to an airway of the user. To stabilize and position the patient interface device on the user, the patient interface device also includes a first contacting member operatively coupled to the support member on a first side of the sealing assembly and a second contacting member operatively coupled to the support member on a second side of the sealing assembly opposite the first side. The first contacting member and the second contacting member are each configured and arranged to contact such a user over a limited contacting region. This limited contacting region corresponds to a junction of the orbicularis oris facial muscle, the zygomaticus facial muscle, and the risorius facial muscle.

It is a further object of the present invention to provide a system for delivering a flow of gas to a user using the patient interface device described above.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural references unless the context clearly dictates otherwise.

BRIEF DESCRIPTION OF THE DRAWINGS

FIGS. 1A, 1B, and 1C are front, side, and bottom exterior views, respectively, of a human face illustrating the exterior location where the contacting members of the patient interface device of the present invention contact the surface of the user;

FIGS. 17-18 are rear and front perspective views, respectively of a third embodiment of a patient interface device according to the principles of the present invention;

DETAILED DESCRIPTION OF THE EXEMPLARY EMBODIMENTS

The present inventors recognized that there are certain locations on the human face that are better suited to support the force needed to hold a patient interface device on the patient than other locations. To take advantage of this, a patient interface device and various embodiments thereof have been developed or proposed that provide a seal around the airway and contact the user at the locations on the patient's face that are best suited to handle the headgear strapping forces.

Figure 1C:
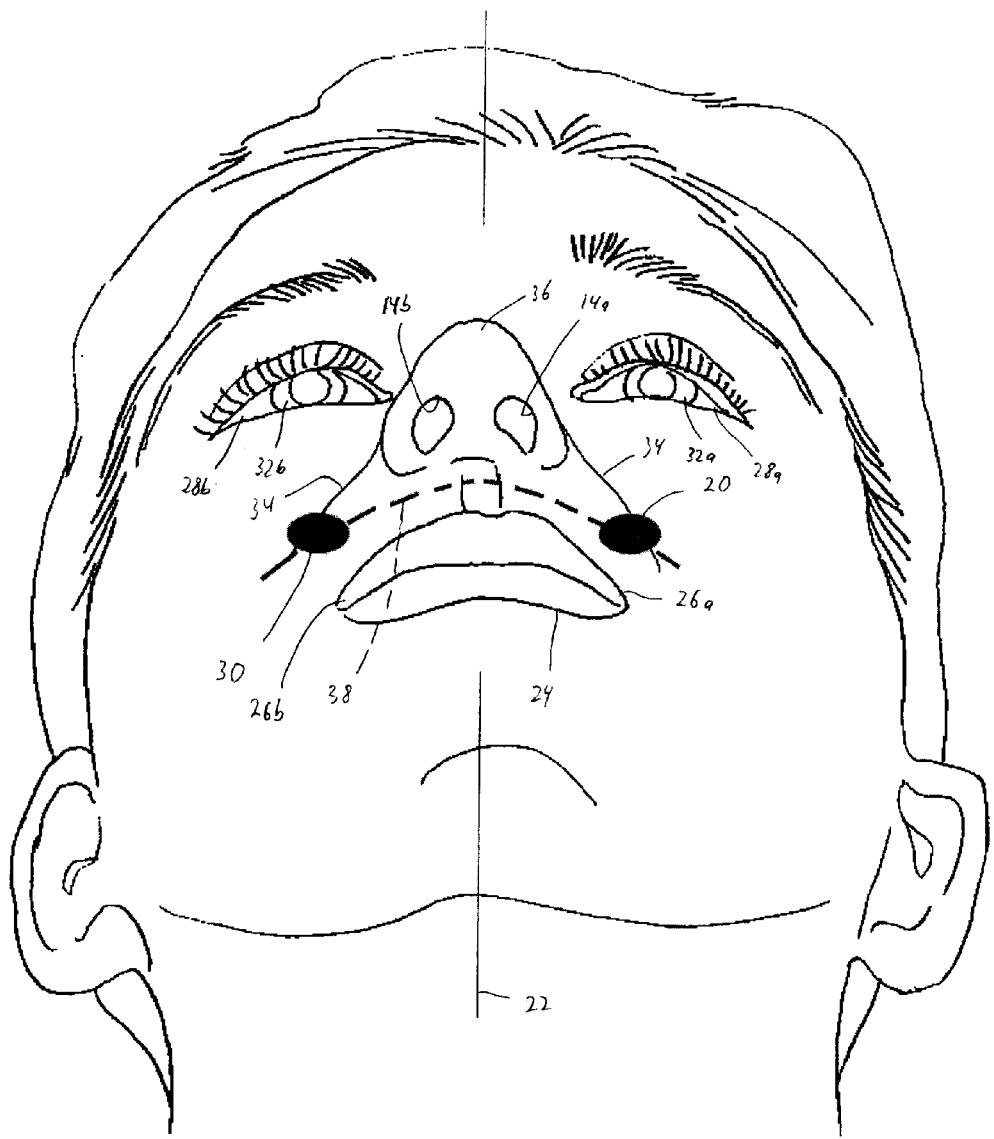
Figure 3:
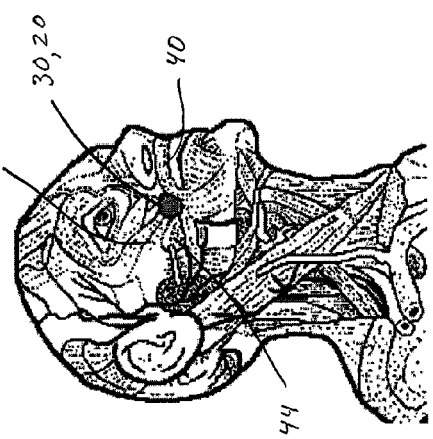
FIG. 3 is a side perspective view the human facial muscles illustrating the location, relative to the facial muscles, where the contacting members are located on the user during normal use.
Figure 4A:
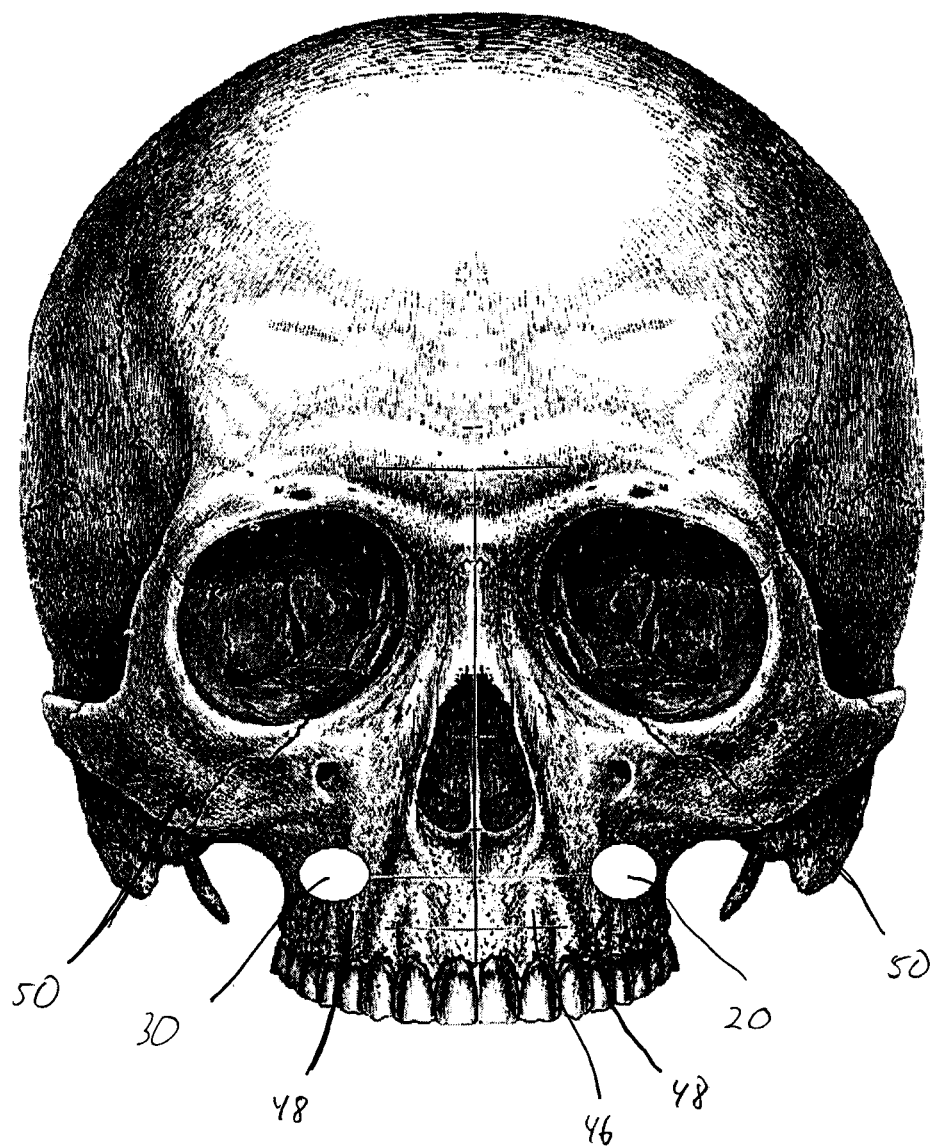
FIGS. 4A and 4B are front and side skeletal views, respectively, of a human skull illustrating the skeletal features where the contacting members are located on the user during normal use.
Figure 4B:
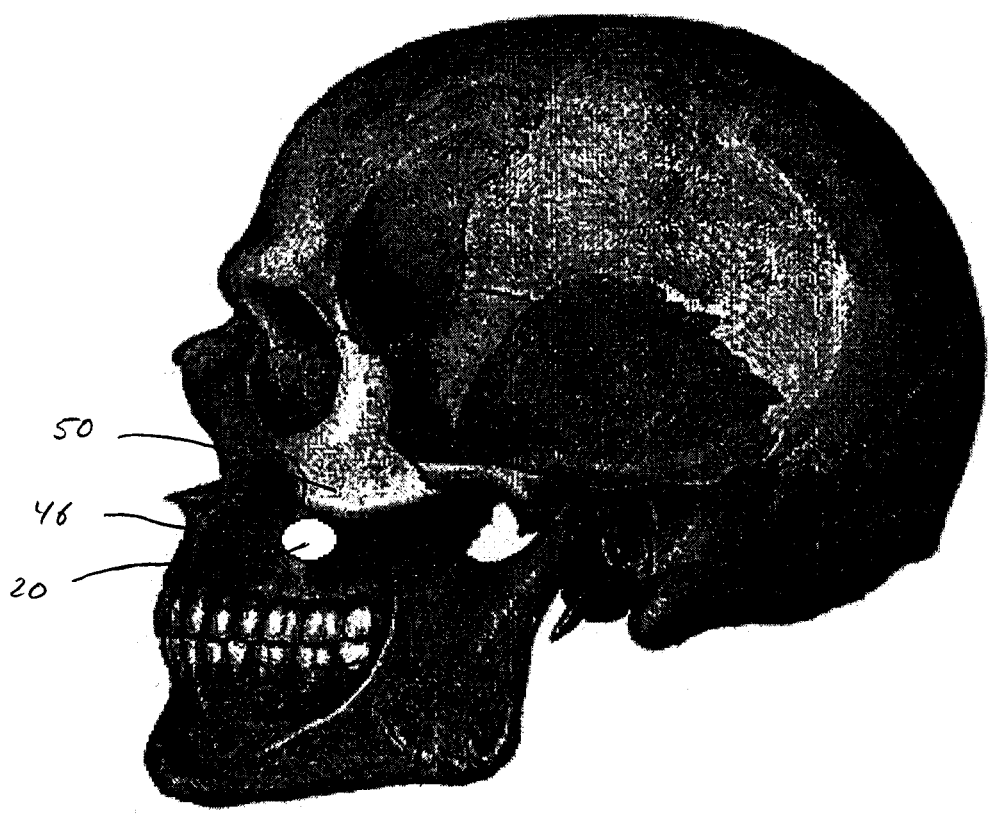
Figure 5:
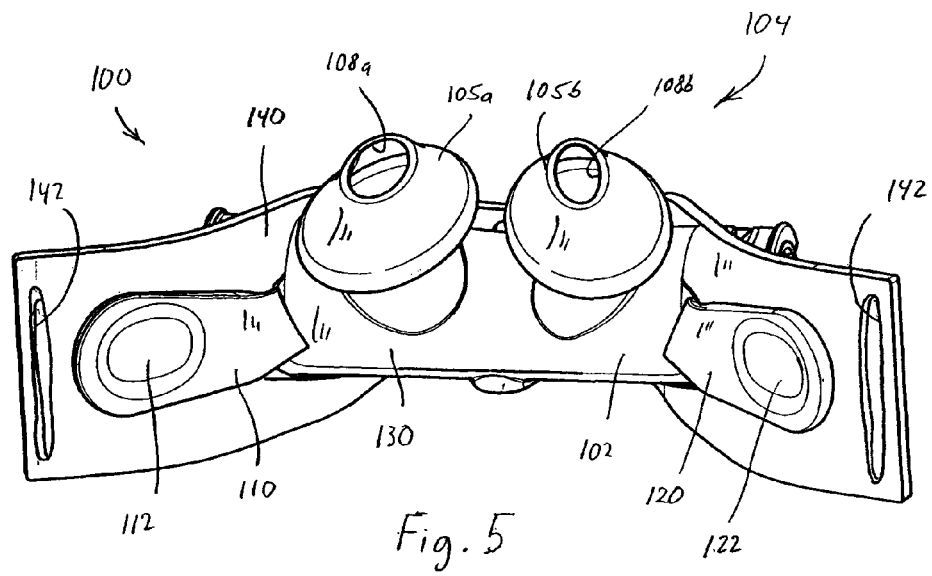
FIGS. 5 and 6 are rear and front perspective views, respectively of a first embodiment of a patient interface device according to the principles of the present invention.

To understand what location on the head/face the present inventors identified and that serves as the location where the patient interface device of the present invention is supported on the user, the human anatomy is considered from both an external view and an internal view. From the internal view, the human anatomy is considered from both the muscular system and the skeletal system. FIGS. 1A and 1B illustrate the exterior view of the human face, FIGS. 2A-2C and 3 illustrate the human facial muscles, and FIGS. 4A and 4B illustrate the skeletal system of the human face. The location of the contacting members is shown as a highlighted region in each figure.

In all these figures, the patient interface device of the present invention includes patient contacting features, such as pads and pad supports described in greater detail below, that contact a first region 20 and a second region 30 on the surface of the user in an area below the eyes and above the mouth. Regions 20 and 30 represent the largest area on the user below the eyes and above the mouth at which the contacting members of the patient interface device contact the user. These regions are disposed on each side of a midline 22 of the head at the front of the face. Please note that FIGS. 1B, 3, and 4B illustrate only one of these two regions due the nature of the illustration being a side view of the human head.

It should be noted that the patient interface device also contacts a portion or the user, typically, but not necessarily near, the airway (such as the nares 14a, 14b, mouth 24, or both), to seal the airway. This is necessary so that a flow of gas can be provided to and received from the user with little or no leakage of gas at the interface between the sealing assembly of the patient interface device and the surface of the user. It should be understood that this sealing function is distinguishable from the support function provided by the contacting members of the patient interface device, which contact first region 20 and second region 30. The support function keeps the patient interface device located on the user at the proper position, and, in particular, keeps the sealing assembly of the patient interface device at the proper orientation, location, angle of attack, etc. relative to the airway. The support function also stabilizes the mask on the surface of the user.

Referring now to FIGS. 1A and 1B, regions 20 and 30 are located above mouth 24, and, more particularly, above each side portion 26a and 26b of the mouth. Regions 20 and 30 are also located below each respective eye 28a and 28b generally offset from iris 32a and 32b toward midline 22. Regions 20 and 30 also generally overlie a nasolabial fold 34, which is the crease that runs from the flanks or sides of nose 26 to the corner of the mouth. The nasolabial fold separates the cheek from the upper lip. When properly positioned, the patient contacting portions generally rest on top of the nasolabial fold in between the nose and the lips.

Regions 20 and 30 also lie generally, but not necessarily completely below the lowest portion of the nose. Regions 20 and 30 do not extend to the mouth, do not touch any part of the nose, and do not extend over the cheeks, or cheek bones, as discussed in greater detail below. In addition, regions 20 and 30 are aligned with one another along an arc 38, that extends below the nose and above the mouth.

Figure 2C:
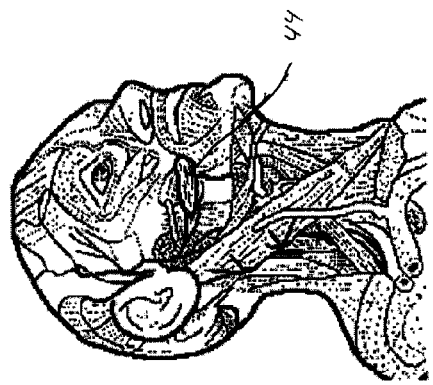
FIGS. 2A-2C are side perspective views of the human facial muscles.
Figure 2B:
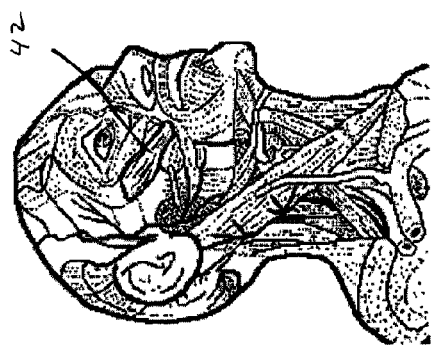
Figure 2A:
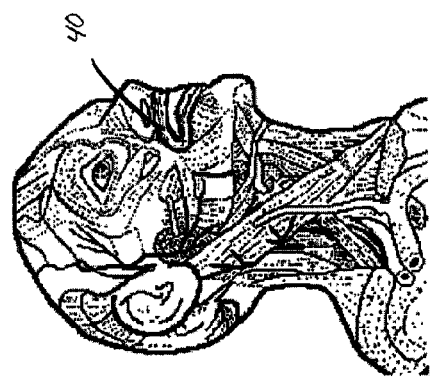

To better understand where regions 20 and 30 are located on the head of the user, reference is now made to FIGS. 2A-2C and C, which illustrate the human facial muscles. Regions 20 and 30 are located at the junction or confluence of the following three facial muscles on each side of the face: (a) the orbicularis oris 40, which is highlighted for illustrative purposes in FIG. 2A; (b) the zygomaticus 42, which is highlighted for illustrative purposes in FIG. 2B; and (c) the risorius 44, which is highlighted for illustrative purposes in FIG. 2C. As shown in FIG. 3, these three muscles converge at a specific region on the human head, which has a generally concave contour. The contacting members (pads, pad supports) in the patient interface device of the present invention are supported on the surface of the user at this location, which is an area approximately 300 mm$^2$ in size and does not extend beyond this area.

FIGS. 4A and 4B illustrate the human facial bones in a still further attempt to describe the location of regions 20 and 30 where the contacting members overlie the skeletal features of the user when the patient interface device is properly positioned on the user. As can be appreciated from reviewing these figures, regions 20 and 30 are provided on maxilla 46 at a canine fossa region 48, which includes the valley at the base of zygomatic bone 50. Regions 20 and 30 can push up against the lower portion of the zygomatic bones but do not overlie the zygomatic bones. It should be emphasized that regions 20 and 30 cover only a limited area on the user, as described above in FIGS. 1A-4B and do not extend beyond this area. Thus, regions 20 and 30 do not overlie the zygomatic bones.

Figure 6:
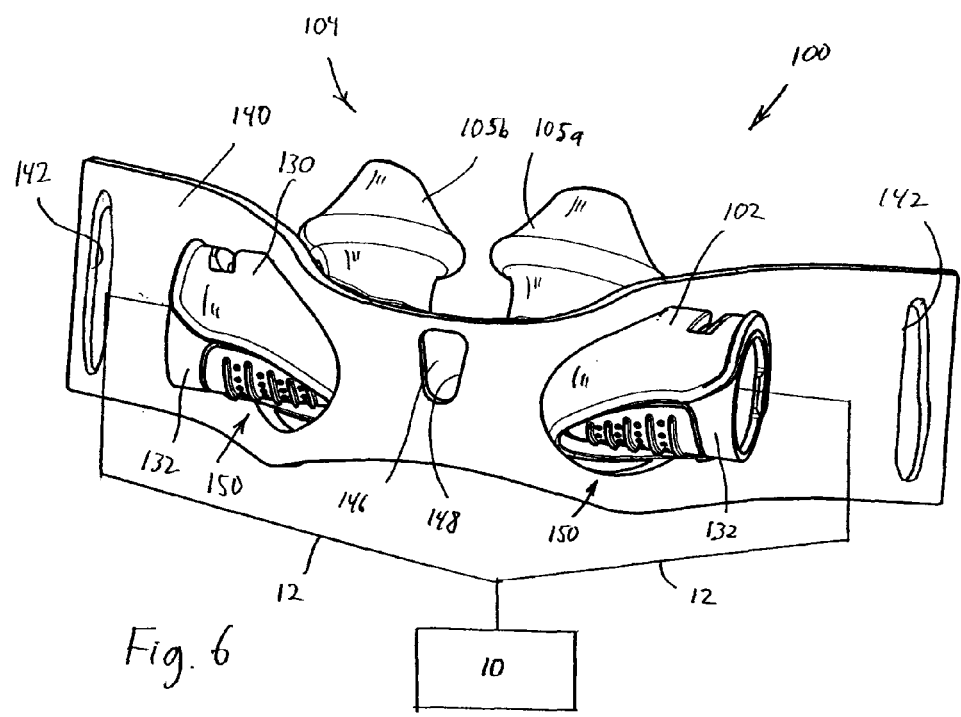
Figure 7:
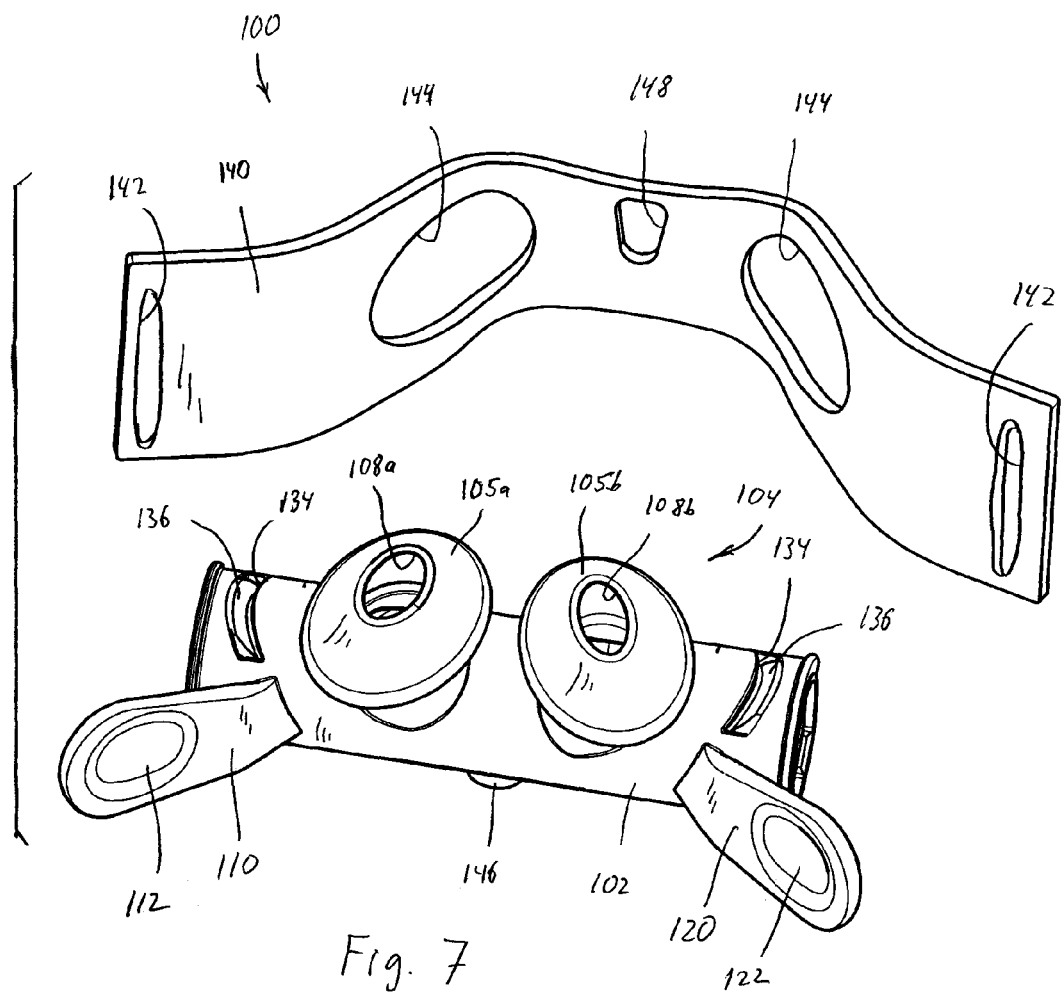
FIG. 7 is an exploded view of the patient interface device of FIG. 5.

FIGS. 5-10 illustrate a first embodiment of a patient interface device 100 according to the principles of the present invention. Patient interface device 100 is shown in FIG. 6 schematically connected to a ventilator or pressure support system 10 via a patient circuit 12, which communicates gas from the pressure support system to the patient interface device. For purposes of the present invention, pressure support system 10 is any conventional ventilation or pressure support system that includes a gas flow generating device capable of delivering a flow of gas to the user. Patient circuit 12 is any device, such as a flexible tubing, that carries the flow of gas from the pressure/flow generator in the pressure support system to the patient interface device. In this schematic illustration, the patient circuit includes a single hose that is coupled to the pressure support system, a Y-connector or Y-junction, and two separate hoses that diverge from the Y-connector and are connected to each side of the patient interface device.

Examples of pressure support systems include, but are not limited to: a ventilator, continuous positive airway pressure (CPAP) device, or a variable pressure device, e.g. an auto-titrating device, proportional assist ventilation (PAV®) device, proportional positive airway pressure (PPAP) device, C-Flex™ device, Bi-Flex® device, or a BiPAP® device manufactured and distributed by Respironics, Inc. of Pittsburgh, Pa., in which the pressure provided to the patient varies with the patient's respiratory cycle so that a higher pressure is delivered during inspiration than during expiration, or other pressure support device.

Patient interface device 100 includes a support member 102 in the form of a tubular portion having an internal passage or lumen 106 that serves as a pathway for the flow of gas to and from the user. In the illustrated embodiment, both ends of support member 102 are coupled to patient circuit 12. However, the present invention also contemplates coupling only one end of the support member to the patient circuit and capping or otherwise blocking or sealing the other end of the support member. A coupling member, such as an elbow joint or flexible sleeve, (not shown in this embodiment) can be provided at the end or ends of support member 102 to couple the support member to the patient circuit.

A sealing assembly 104 is operatively coupled to support member 102. In the embodiment of FIGS. 5-10, sealing assembly 104 is a pair of nasal prongs 105a and 105b that seal against the nares of the user. A gas flow path 106 is provided in support member 102 and openings 108a and 108b are provided in each prong to communicate gas from the pressure/flow generating system to the airway of the user when the patient interface device is donned by the user. In the illustrated embodiment, each prong has a general "mushroom" configuration with a stem portion and a head portion, both of which are formed from a flexible material, such as silicon. Of course, the portions of the prongs can be formed from different materials. For example, the head can be formed of foam or gel and the stem formed from silicon. In addition, the nasal prongs can have a variety of configurations, such as dome-shaped, and can have other features, such as bellows, pleats, and grooves that enable the position, orientation, or angle of the prongs to move or be adjusted to match the anatomical features of the user. Examples of other nasal prongs suitable for use in the sealing assembly of the present invention are described in U.S. patent application Ser. No. 11/074,410 (publication no. 20050199242)("the '410 application") the contents of which are incorporated herein by reference and in U.S. patent application Ser. No. 11/048,680 (publication no. US-2005-0205096-A1) the contents of which are incorporated herein by reference.

A first contacting member 110 is operatively coupled to support member 102 on a first side of sealing assembly 104. Likewise, a second contacting member 120 is operatively coupled to the support member on an opposite side of the sealing assembly from the first side. First contacting member 110 is configured and arranged to contact a user over only region 20, as defined above with respect to FIGS. 1-4B. Similarly, second contacting member 120 is configured and arranged to contact a user over only region 30, as defined above.

A first pad 112 is provided on first contacting member 110, and a second pad 122 is provided on second contacting member 120. Pads 112 and 122 are shaped, sized, and configured to contact only regions 20 and 30 noted above. The pads are joined to the contacting member, permanently or removably, using any conventional technique. For example, the pads can be adhered to the contacting members to provide a permanent attachment. The pads and contacting members can be configured such that the pads snap onto or slip onto the contacting members. Pads 112 and 122 can be made from any suitable material or combination of materials, such as gel, foam, silicon. Example of gel materials suitable for use as pads 112 and 122 are described in U.S. Pat. Nos. 5,647,357; 5,884,624; 6,397,847; and 6,895,965 and pending U.S. provisional patent application Ser. No. 11/715,760 ("the '760 application")(collectively referred to as "the gel references"), the contents of each of which are incorporated herein by reference. The present invention contemplates that pads 112 and 122 can be omitted. In which case, the surface of first and second contacting members 110 and 120 can be configured so as to be comfortable to the user.

Figure 8:
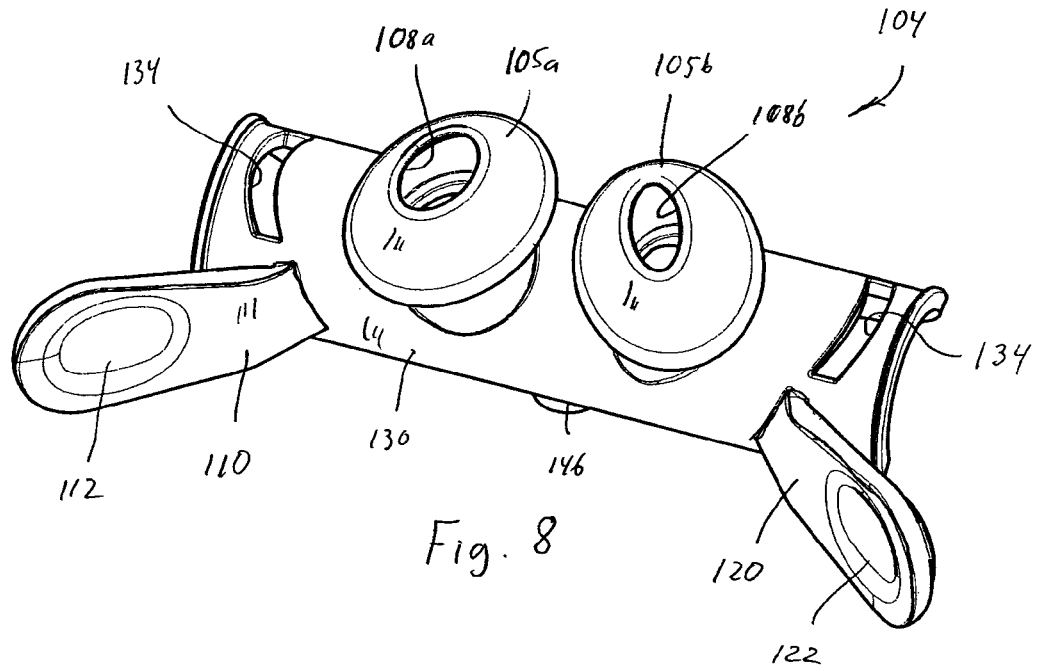
FIGS. 8-10 are rear, front, and size perspective views, respectively, of the support member, sealing assembly, and contacting members in the patient interface device of FIG. 5.
Figure 9:
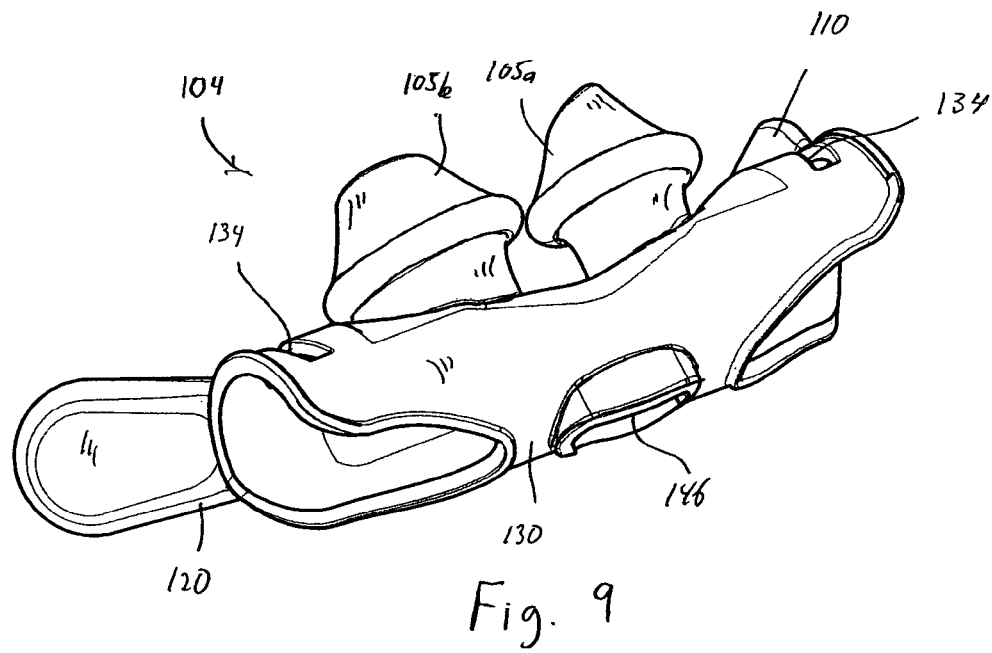
Figure 10:
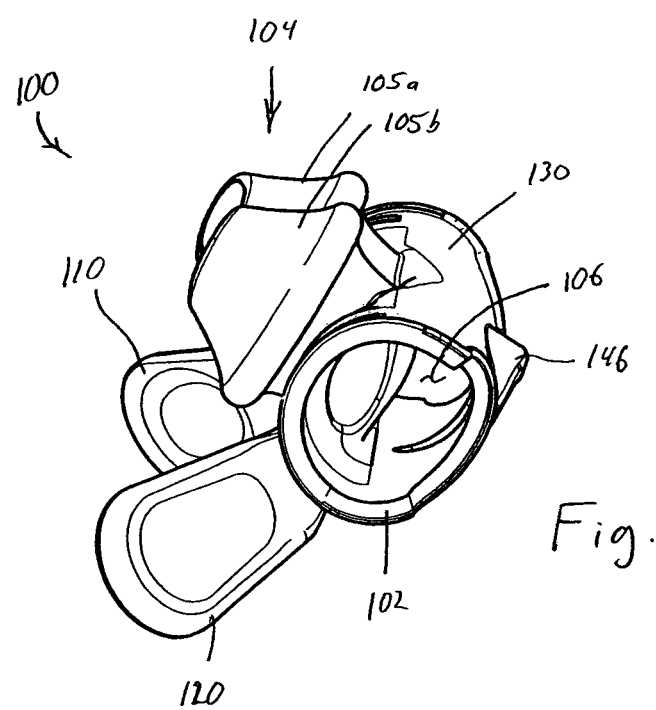
Figure 11:
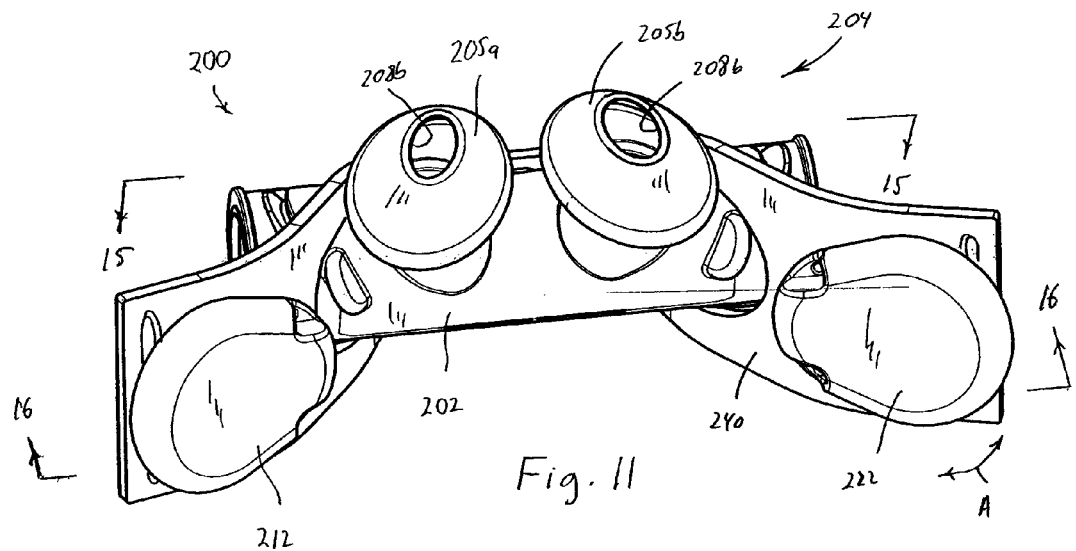
FIGS. 11 and 12 are rear and front perspective views, respectively of a second embodiment of a patient interface device according to the principles of the present invention.
Figure 12:
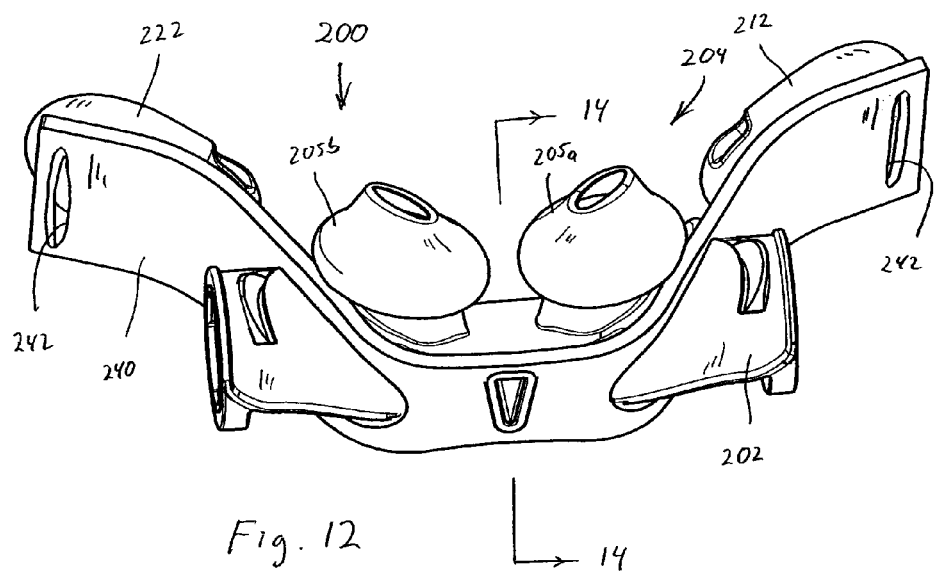
Figure 13:
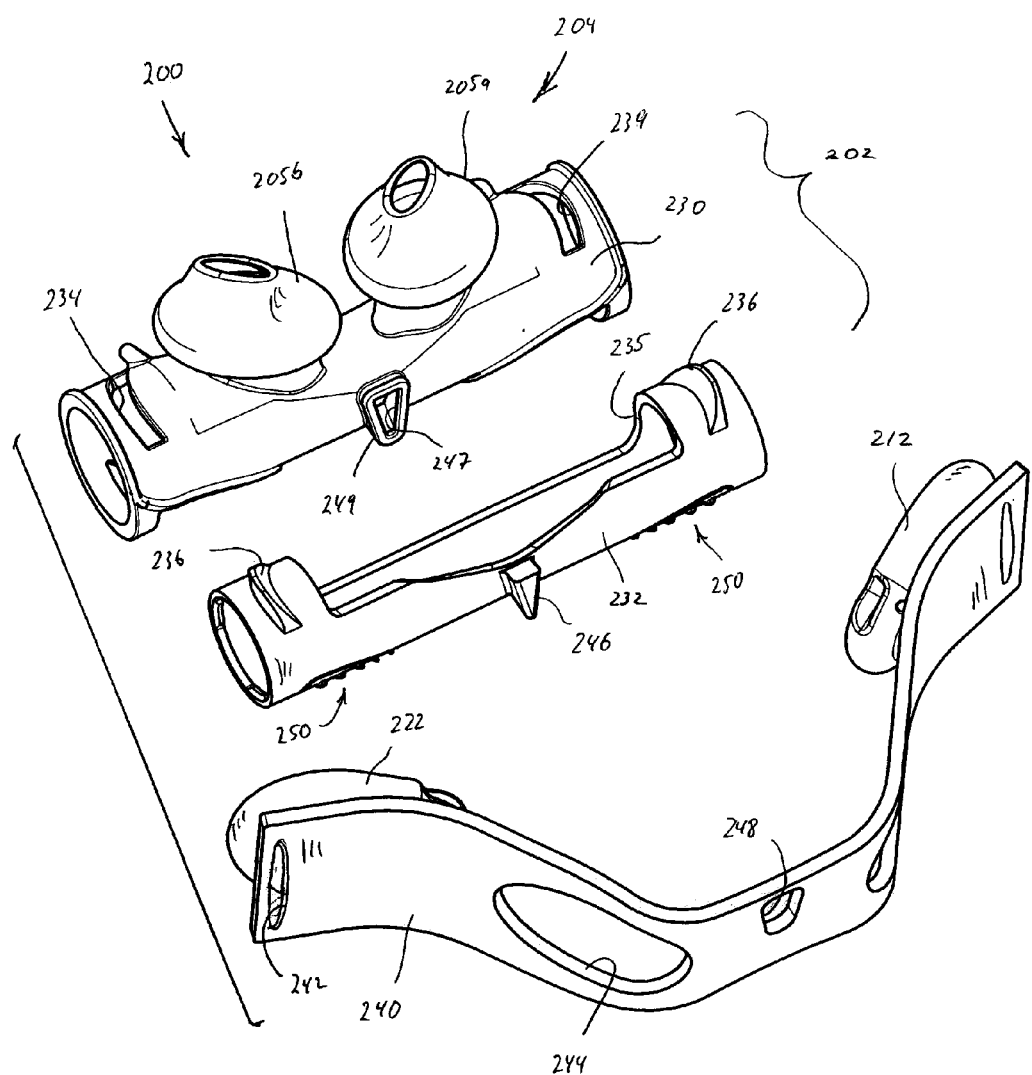
FIG. 13 is an exploded view of the patient interface device of FIG. 11.
Figure 14:
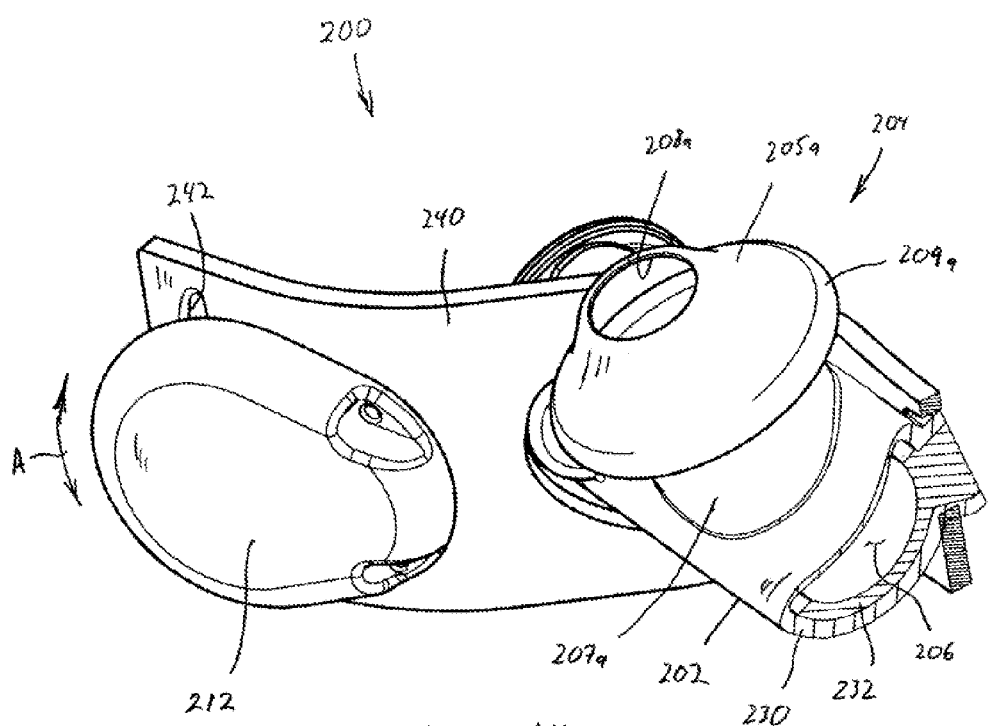
FIG. 14 is a cross-sectional view of the patient interface device of FIG. 11 taken alone line 14-14 of FIG. 12.
Figure 15:
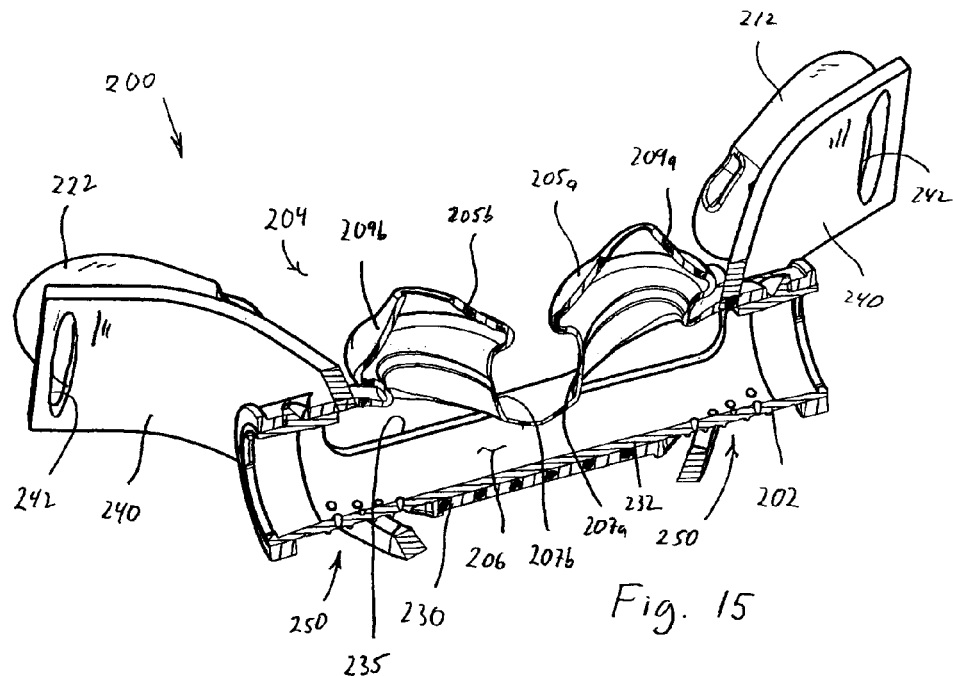
FIG. 15 is a cross-sectional view of the patient interface device of FIG. 11 taken alone line 15-15 of FIG. 11.
Figure 16:
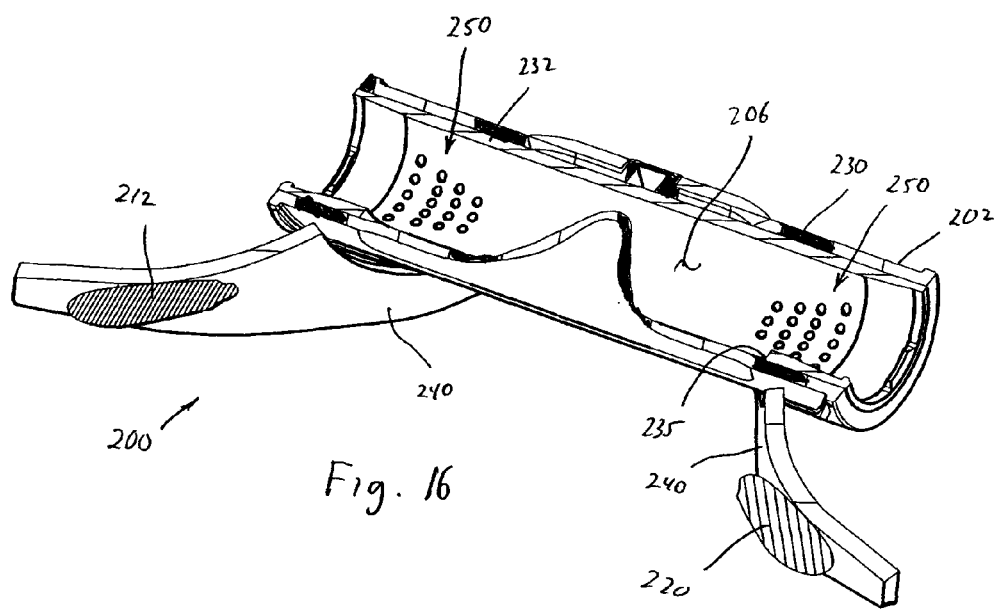
FIG. 16 is a cross-sectional view of the patient interface device of FIG. 11 taken alone line 16-16 of FIG. 11.
Figure 19:
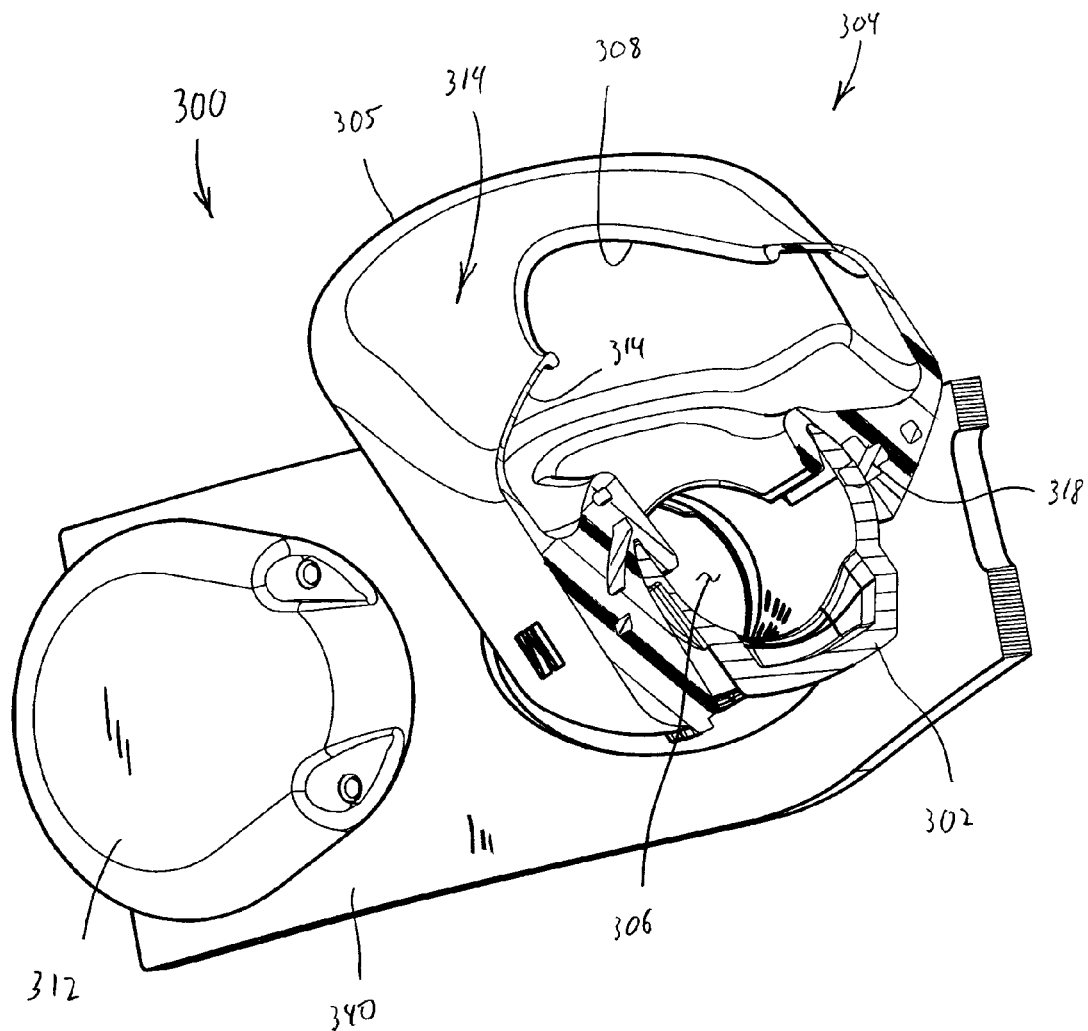
FIG. 19 is a cross-sectional view of the patient interface device of FIG. 17 taken alone line 19-19 of FIG. 17.
Figure 20:
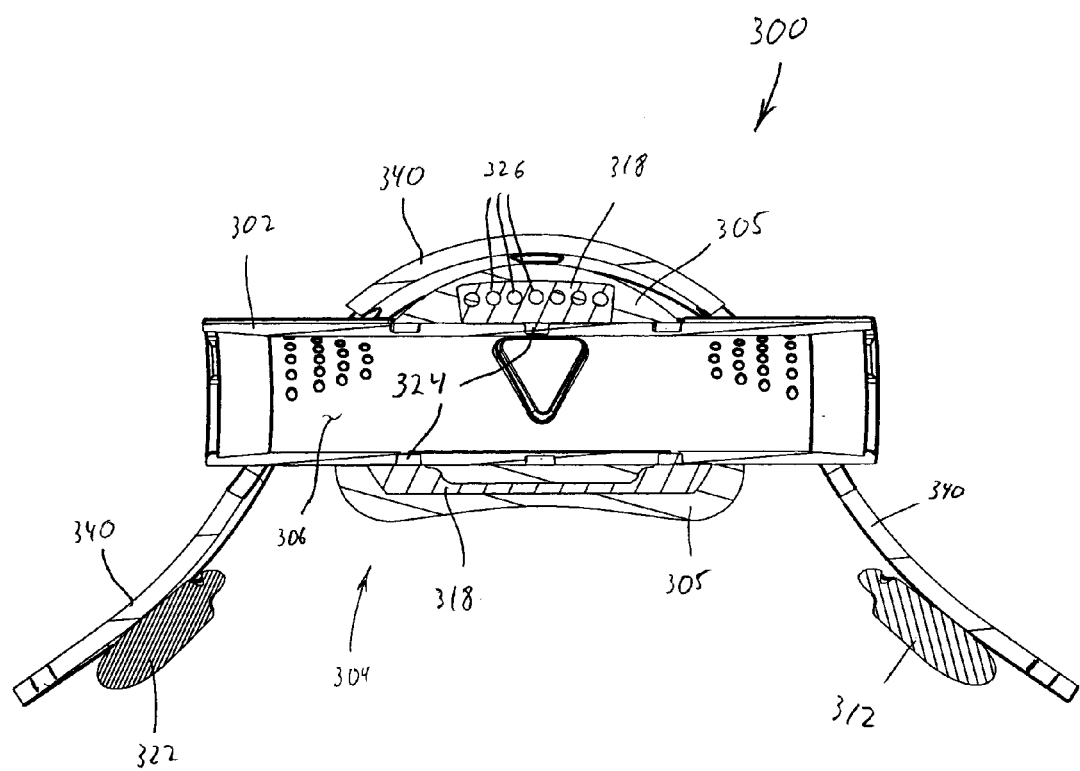
FIG. 20 is a cross-sectional view of the patient interface device of FIG. 17 taken alone line 20-20 of FIG. 17.

In the illustrated embodiment, first and second contacting members 110 and 120 are generally flexible or semi-rigid members so that they can deform as the patient interface device is forced against the surface of the user, typically by tightening the headgear. The present invention contemplates that first and second contacting members 110 and 120 are connected to support member 102 using any conventional technique. In the embodiment of FIGS. 5-10, the first and second contacting members are integral with support member 102, for example, by forming both at least a portion of the support member and the contacting members from a common material. Indeed, the present invention even further contemplates forming at least a portion of support member 102, sealing assembly 104, and contacting members 110 and 120 as a unitary element 130, an example of which is shown in FIGS. 8-10.

In an exemplary embodiment, unitary element 130 is an injection molded part that is formed from a flexible material, such as silicon. This provides the flexibility needed for sealing assembly 104 and contacting members 110, 120. However, in an exemplary embodiment, support member 102 is formed from a rigid or semi-rigid material, so as to provide structural integrity for the patient interface device. To provide structural support for support member 102 in this embodiment, a support element 132, which is rigid or semi-rigid member, is provided as a component of the support member. The support member is formed by assembling support element 132 within unitary element 130, for example, by inserting the support element into the unitary element. In an exemplary embodiment, support element 132 is formed from a rigid plastic and is generally tubular.

To maintain unitary element 130 in an assembled relation with support element 132, the present invention contemplates providing an attachment/alignment mechanism for engaging these two elements together. In this embodiment, grooves 134 are provided in unitary element 130 and protrusions 136 are provided in support element 132. When the unitary element is properly assembled with the support element, protrusions 134 are seated in grooves 134. Thus, the protrusions and grooves also serve to ensure that unitary element 130 is properly aligned on or attached to support element 132. It is to be understood that the present invention contemplates using any conventional technique for attaching unitary element 130 with support element 132, such a clamps, friction fitting, adhesive, bonds, or welds. In addition, the size, shape, configuration and location of the protrusions 136 and grooves 134 can be varied, including providing the grooves in support element 132 and providing the protrusion on unitary element 130.

To couple a headgear (not shown) to patient interface device 100, the patient interface device of the present embodiment includes a support frame 140 that is operatively coupled to support member 102. The headgear, and, in particular, the headgear straps, attach to support frame 140 using any conventional technique. In the illustrated embodiment, slots 142 are provided into which the headgear straps insert. Of course, any fastening technique for joining the headgear strap to the support frame are contemplated by the present invention, including snaps, hooks, loops, clamps, or other connectors. Examples of fastening techniques suitable for use with the present invention are described in U.S. patent application Ser. No. 10/629,366 (publication no. US-2004-0025883-A1) ("the '366 application"), the contents of which are incorporated herein by reference.

Support frame 140 can be rigid, semi-rigid, or even non-rigid structure so long as it accomplishes the function of translating the strapping force of the headgear to the patient contacting portions of the patient interface device, i.e., sealing assembly 104 and contacting member 110, 120. Support frame 140 can be coupled to support member 102 in any manner. However, in the illustrated embodiment, the support member is inserted into openings 144 provided in the support frame.

To ensure that support member 102 is properly assembled with support frame 140, the present invention contemplates providing an alignment mechanism that orients the support member to the support frame. In the illustrated embodiment, the alignment mechanism includes a protrusion 146 is provided on support member 102 and an opening or slot 148 is provided on support frame 140. To properly assemble the support member to the support frame, the protrusion is seated in slot 148. This is accomplished, for example, by rotating the support member in the support frame and/or sliding one relative to another until alignment is reached. It is to be understood that the present invention contemplates using any conventional technique for attaching support member 102 with support frame 140, such a clamps, friction fitting, adhesive, bonds, or welds. In addition, the size, shape, configuration and location of the protrusions 146 and slot 148 can be varied, including providing the opening in support member 102 and providing the protrusion on the support frame 140.

Patient interface device 100 includes an exhaust assembly 150 to vent gas from the interior of the patient interface device to ambient atmosphere, which is necessary in a non-invasive type of gas delivery system. The present invention contemplates that exhaust assembly 150 can have any configuration, so long as the function of exhausting a sufficient amount of gas to atmosphere is achieved. For example, the exhaust assembly can be configured to provide a continuous flow rate for the venting of exhaust gas to atmosphere, or can be configured to provide a variable flow rate; dependent, for example, on the pressure of the gas in the closed system.

In the illustrated embodiment, exhaust assembly 150 is defined by a plurality of vent holes provided in the wall of support member 102. The number, size, hole pattern, and shape of the holes can have any configuration. One example of a multiple-hole type of exhaust assembly suitable for use in the present invention is disclosed in U.S. patent application Ser. No. 10/119,673 (publication no. 2003/0005931), the contents of which are incorporated herein by reference. It should also be noted that only one exhaust assembly need be provided on the patient interface device, so long as the exhaust flow rate is sufficient to provide an adequate exhaust gas venting function. The exhaust assembly can also be omitted if exhausting gas from the system is not needed or if the exhaust assembly is provided elsewhere, such as in the patient circuit.

FIGS. 11-16 illustrate a second embodiment of a patient interface device 200 according to the principles of the present invention. Patient interface device 200 includes a support member 202 and a sealing assembly 204 coupled to support member. Support member 202 includes an internal passage or lumen 206 that serves as a pathway for the flow of gas to and from the user. As in the previous embodiment, one or both ends of support member 202 are coupled to a pressure support system.

Sealing assembly 204 is a pair of nasal prongs 205a and 205b with openings 208a and 208b provided in each prong to communicate gas in lumen 206 to the airway of the user. As in the previous embodiment, each prong has a "mushroom" configuration with a stem portion 207a, 207b and a head portion 209, 209b. Of course, other embodiments for the nasal prongs, as well as the entire sealing assembly are contemplated by the present invention. For example, the sealing assemblies set forth in subsequent embodiments are contemplated for use in the present embodiment.

A unitary element 230 in combination with a support element 232 define support member 202. An opening 235 is provided in support element 232, and unitary element 230 is configured to fit over the opening in the support element and enclose the opening. This same configuration can be used in the previous embodiment. In an exemplary embodiment of the present invention, unitary element 230 is formed form a flexible material and support member 202 is formed from a rigid material. In addition, unitary element 230 is configured so as to dip into opening 235, as perhaps best shown in FIGS. 14-16, to keep the profile of the patient interface as small as possible.

To connect and align unitary element 230 with support element 232, grooves 234 are provided in the unitary element and protrusions 236 are provided in the support element. When the unitary element is properly assembled with the support element, protrusions 234 are seated in grooves 234. Of course, other techniques for mating the support element to the unitary element are contemplated by the present invention. In addition, it is to be understood that grooves 234 and protrusions 236 can be omitted entirely. Exhaust assemblies 250, in the form of a plurality of vent holes defined in the wall of support member 202, are provided to vent gas from the interior of the patient interface device to ambient atmosphere.

As in the previous embodiment, a support frame 240 is coupled to support member 202. A headgear (not shown) is coupled to the support frame via slots 242. Of course, any technique for attaching the headgear to the support frame is contemplated by the present invention. In this embodiment, the first and second contacting members are eliminated in favor of coupling a first pad 212 and a second pad 222 to support frame 240. Pads 212 and 222 are shaped, sized, and configured to contact only region 20, 30 in the face of the user and are joined to the support frame, permanently or removably, using any conventional technique. In addition, pads 212 and 222 can be made from any suitable material, such as gel, foam, silicon. The present invention also contemplates that the pads are rotatably coupled to the support frame such that they rotate as indicated by arrow A.

Support frame 240 can be rigid, semi-rigid, a non-rigid structure, or any combination thereof so long as it accomplishes the function of translating the strapping force of the headgear to the patient contacting portions of the patient interface device, i.e., sealing assembly 204 and pads 212 and 222. Protrusions 236 can be used to help maintain the support frame on the support member by extending the protrusions beyond the surface of the support member to server as a stopper for outward movement of the support member.

Support frame 240 is coupled to support member 202 in any suitable manner. However, in the illustrated embodiment, the support member is inserted into openings 244 provided in the support frame. A protrusion 246 is provided on support element 232 and an opening or slot 247 is provided in unitary element 230 to receive the protrusion. In addition, a further opening or slot 248 is provided in support frame 140. To properly assemble support member 202 to the support frame, protrusion 246 is seated in slot 248. In this embodiment, walls 249 are provided around slot 247, which also insert into slot 248.

FIGS. 17-21 illustrate a third embodiment of a patient interface device 300 according to the principles of the present invention. This embodiment is generally similar to that of FIGS. 11-16 in that a sealing assembly 304 is mounted onto a support member 302, and first and second pads 312 and 322 are coupled to the support member via a support frame 340 that is also attached to the support member.

In this embodiment sealing, however, assembly 304 takes the form of a single cushion 305 attached or attachable to the support member, rather than a pair of nasal prongs or cannulae. Support member 302 is a rigid, semi-rigid, or flexible tube having a cylindrical shape with a passage 306 defined therein. Of course, other shapes and configurations for support member are contemplated by the present invention.

Cushion 305 is sized and configured to seal around the nares of the user and includes a single opening 308 to communicate the user's airway with passage 306 in support member 302. Thus, the area of contact between the sealing portion of the patient interface device and the surface of the user is limited. As example of a cushion suitable for use in the present invention that seals in this area is described in the '410 application and in U.S. Pat. No. 5,742,965, the contents of which are incorporated herein by reference. A patient contacting surface 314 of cushion 305 is contoured, e.g., saddle-shaped, to match, at least generally, the surface of the user around the nose.

Cushion 305 can be made from any suitable material, such as gel (see the gel references), silicone, foam, rubber, or combination of materials. Cushion 305 can also be formed from a highly elastic material, such that that disclosed in U.S. patent application Ser. No. 11/266,808, the contents of which are incorporated herein by reference. The present invention further contemplates that cushion 305 includes one or more flaps provided at a patient contacting portion of the cushion. Note that only one flap 316 is show in the figures. An example of a cushion having multiple flaps is disclosed in U.S. Pat. No. 4,971,051, the contents of which are incorporated herein by reference. Furthermore, cushion 305 can include other structures, such as ribs, support members, varying wall thickness, and pleats to control the sealing characteristic of the cushion. As example, of a cushion having pleats suitable for use in the present invention is disclosed in U.S. patent application Ser. No. 11/312,026 (publication no. 20060130844), the contents of which are incorporated herein by reference.

Figure 37:
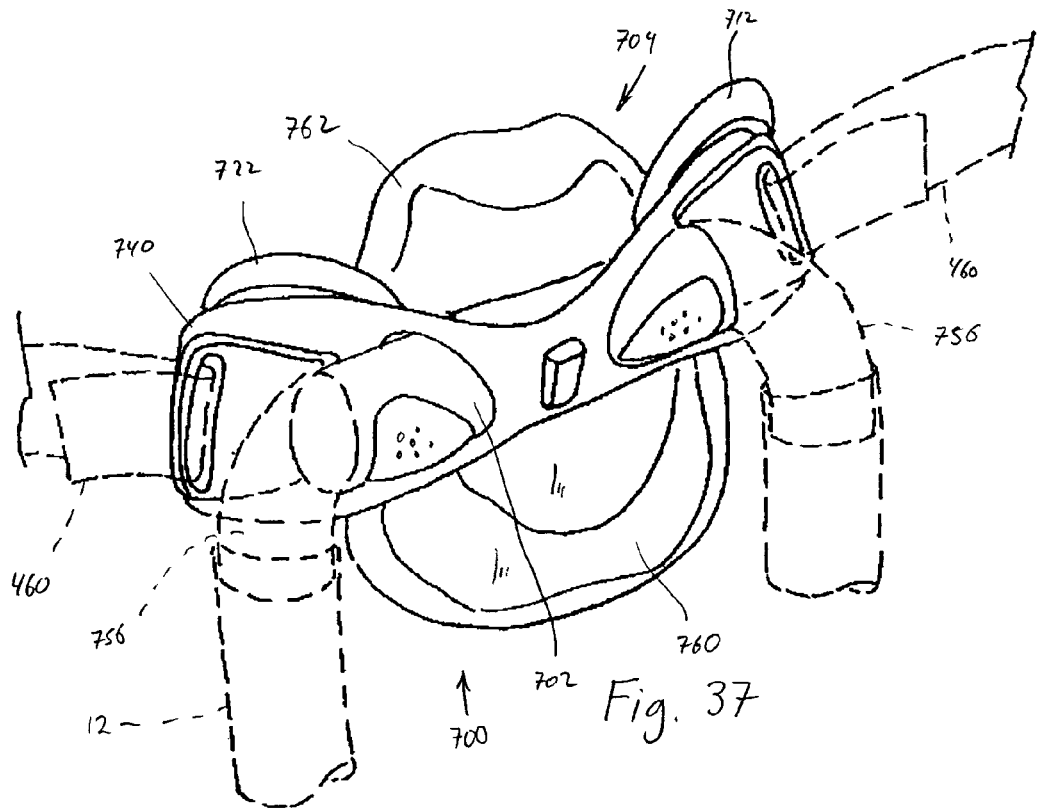
FIGS. 37 and 38 are front and rear perspective views, respectively, of a seventh embodiment of a patient interface device according to the principles of the present invention.
Figure 38:
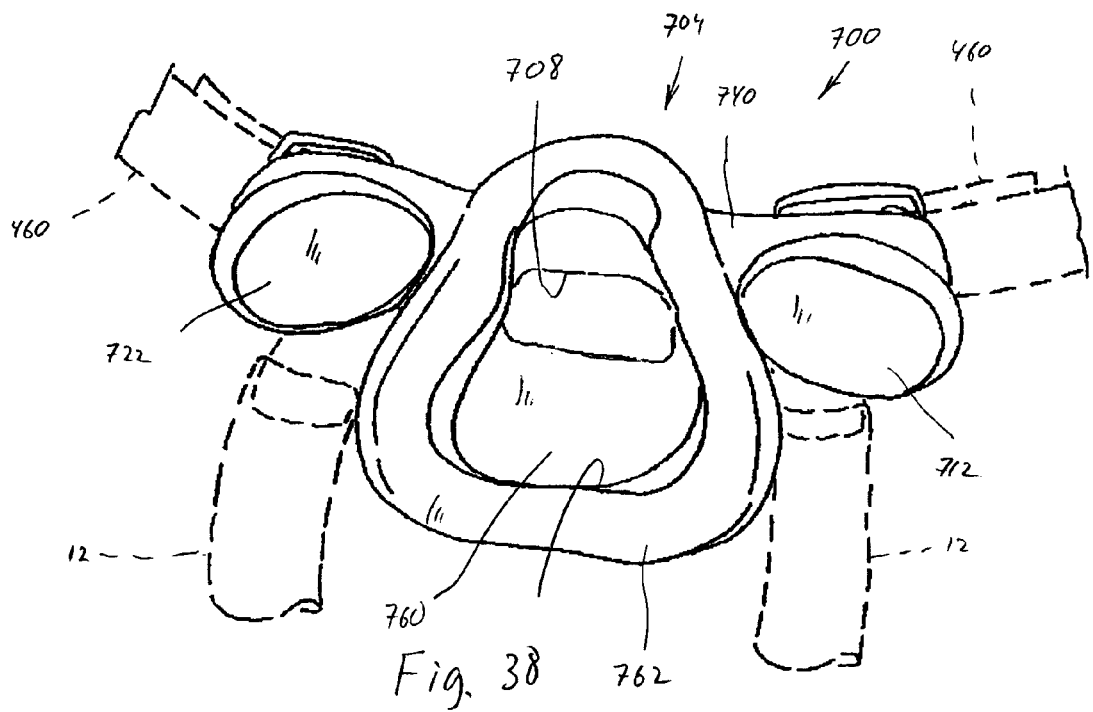

It is to be further understood that the cushion 305 can have other sizes and configurations and overlie or seal against other portions of the user, in particular, the face of the user. FIGS. 37 and 38, for example, describe a cushion having a sealing area that extends over the nose and/or around the mouth.

Cushion 305 can be attached to support member 302 using any conventional technique. However, in the illustrated embodiment, the cushion is attached to the support member by means of a coupling structure 318 provided in or coupled to cushion 305. More specifically, coupling structure 318 is a rigid or semi-rigid member that is embedded in the material forming the cushion. A portion or portions of the coupling structure, such as tabs 324, extend from the cushion to engage a groove or grooves provided in the support member.

The coupling structure and the cushion are coupled to one another in any conventional manner. However, in an exemplary embodiment, the cushion is molded over the coupling structure. To ensure a secure attachment of the cushion to coupling structure 318, a plurality of openings 326 are formed in the coupling structure so that the material defining the cushion can flow into these openings during the cushion molding process. An example of a cushion and coupling structure suitable for use in the present invention to attach the cushion to the support member is disclosed in U.S. patent application Ser. No. 11/374,942 (publication no.

Figure 29:
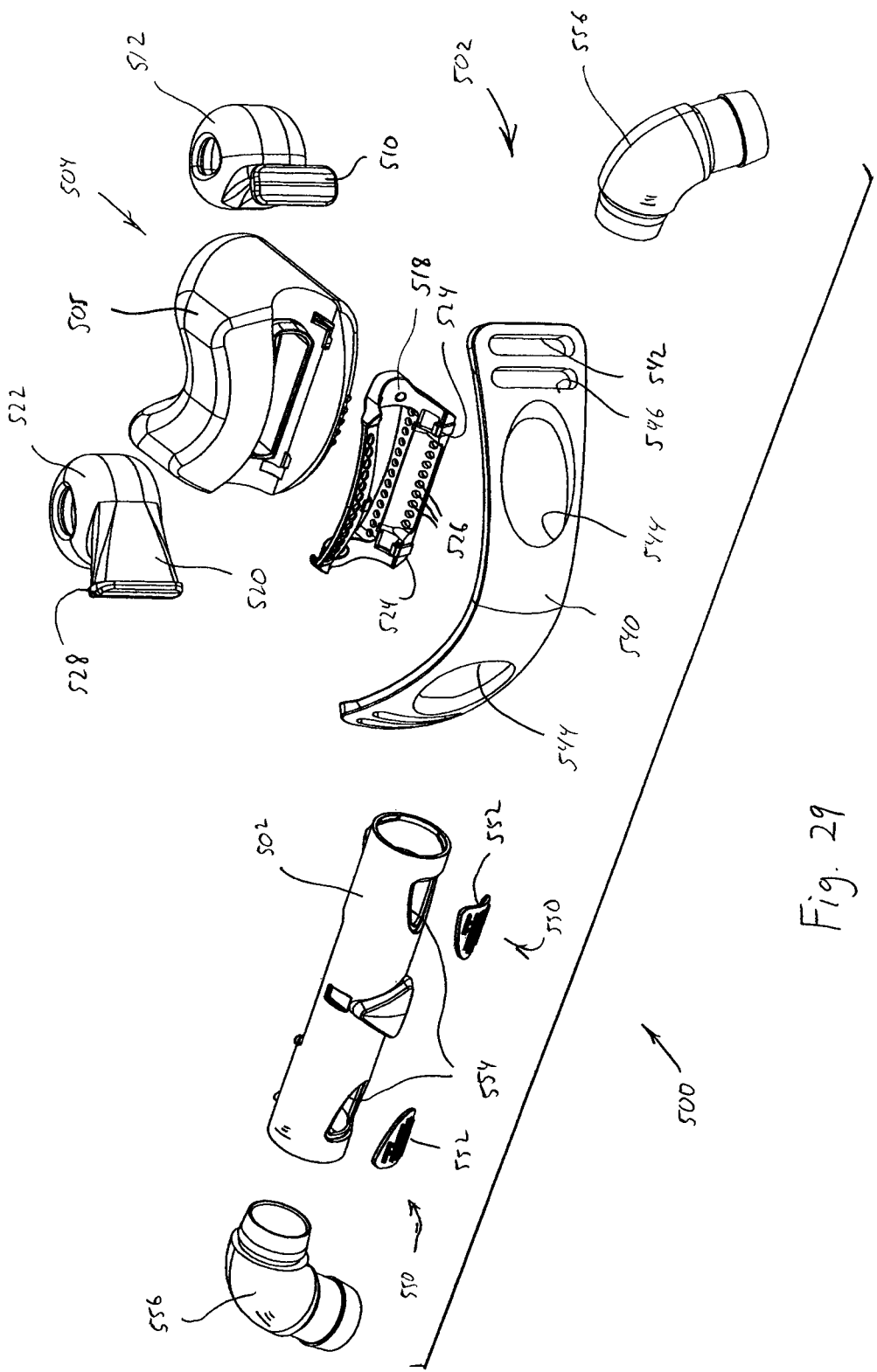
FIG. 29 is an exploded view of the patient interface device of FIG. 27.
Figure 30:
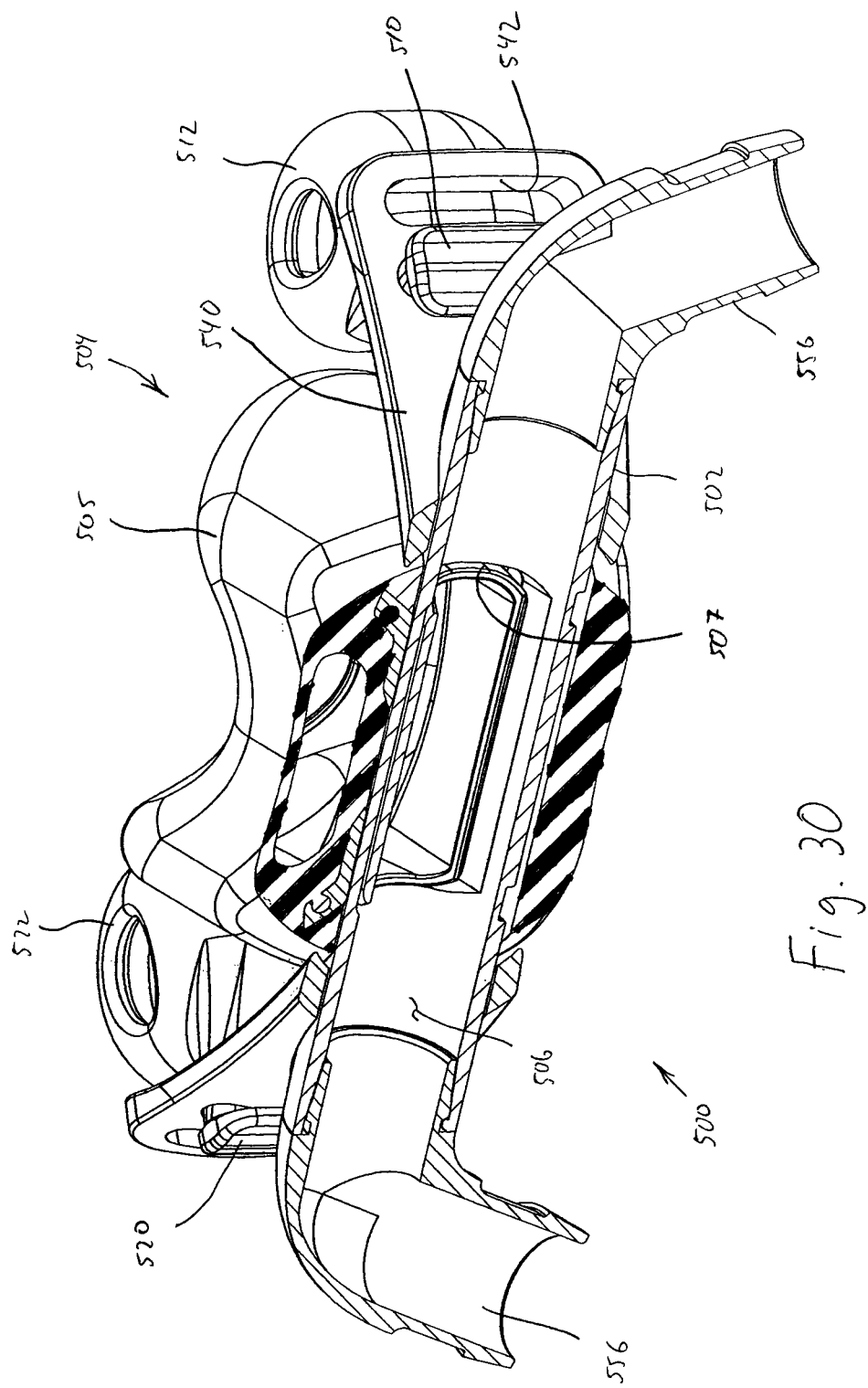
FIG. 30 is a cross-sectional view of the patient interface device of FIG. 27 taken alone line 30-30 of FIG. 28.
Figure 31:
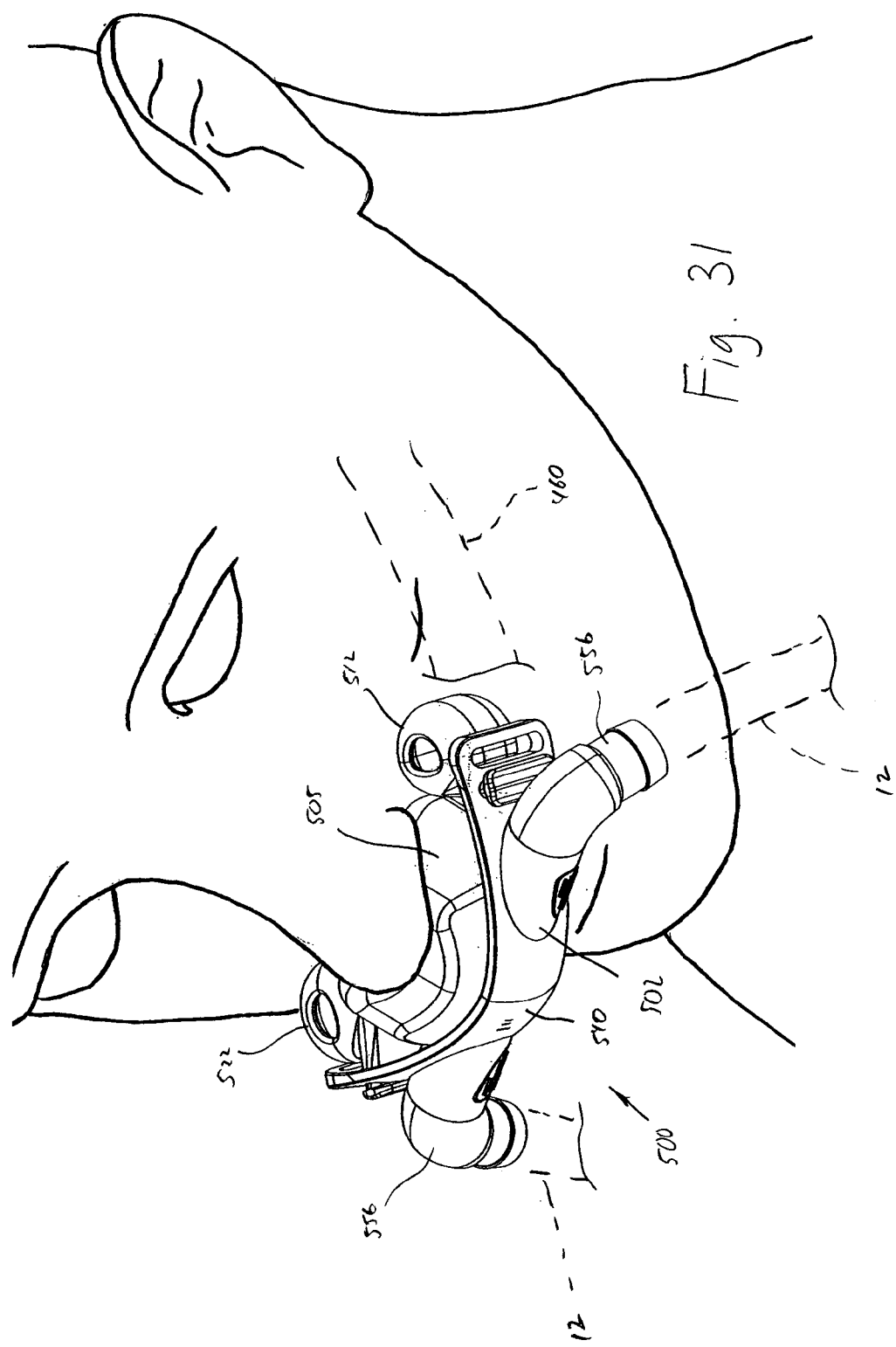
FIG. 31 is a perspective view showing a patient wearing the patient interface device of FIG. 27.
Figure 32:
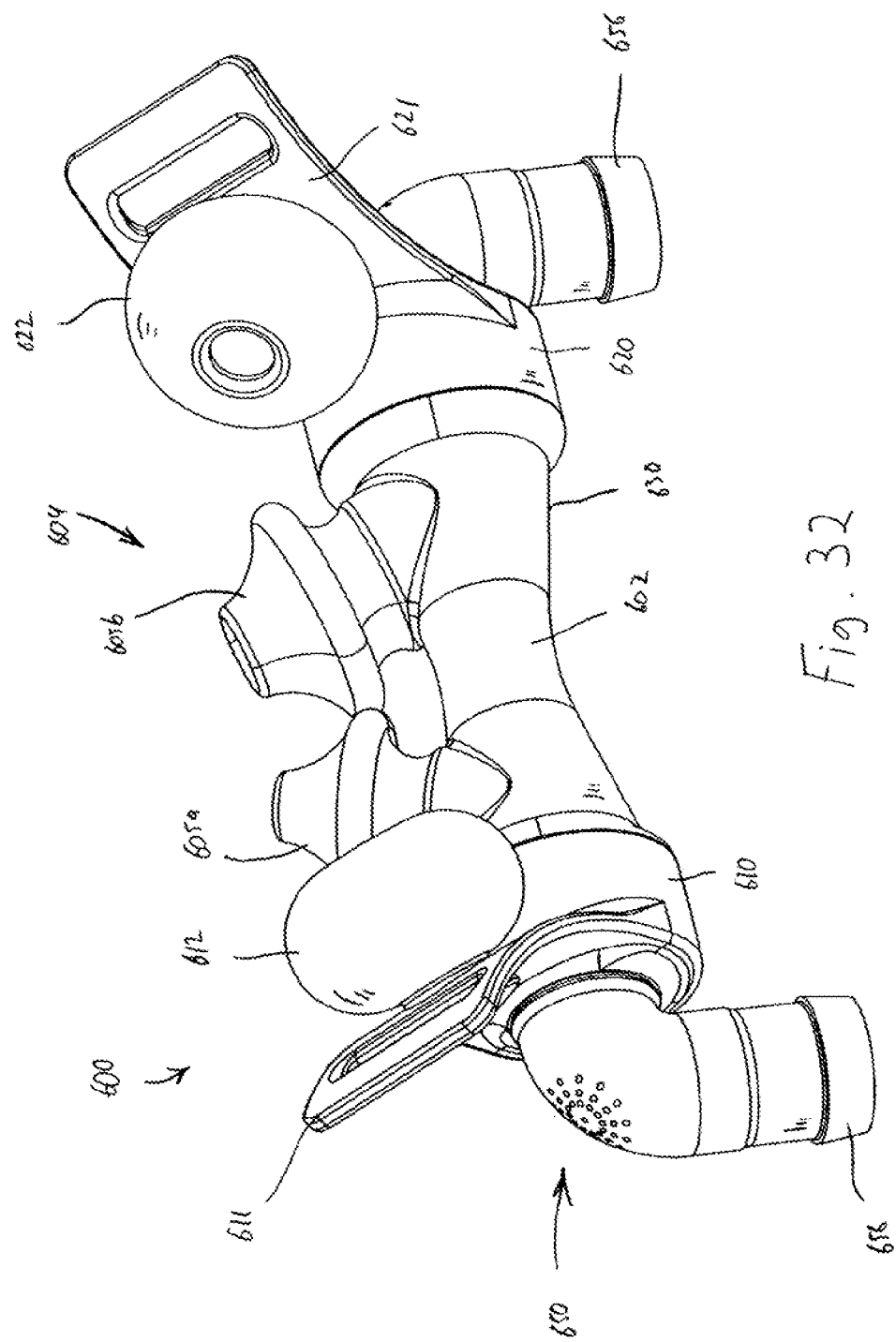
FIGS. 32 and 33 are rear and front perspective views, respectively, of a sixth embodiment of a patient interface device according to the principles of the present invention.
Figure 33:
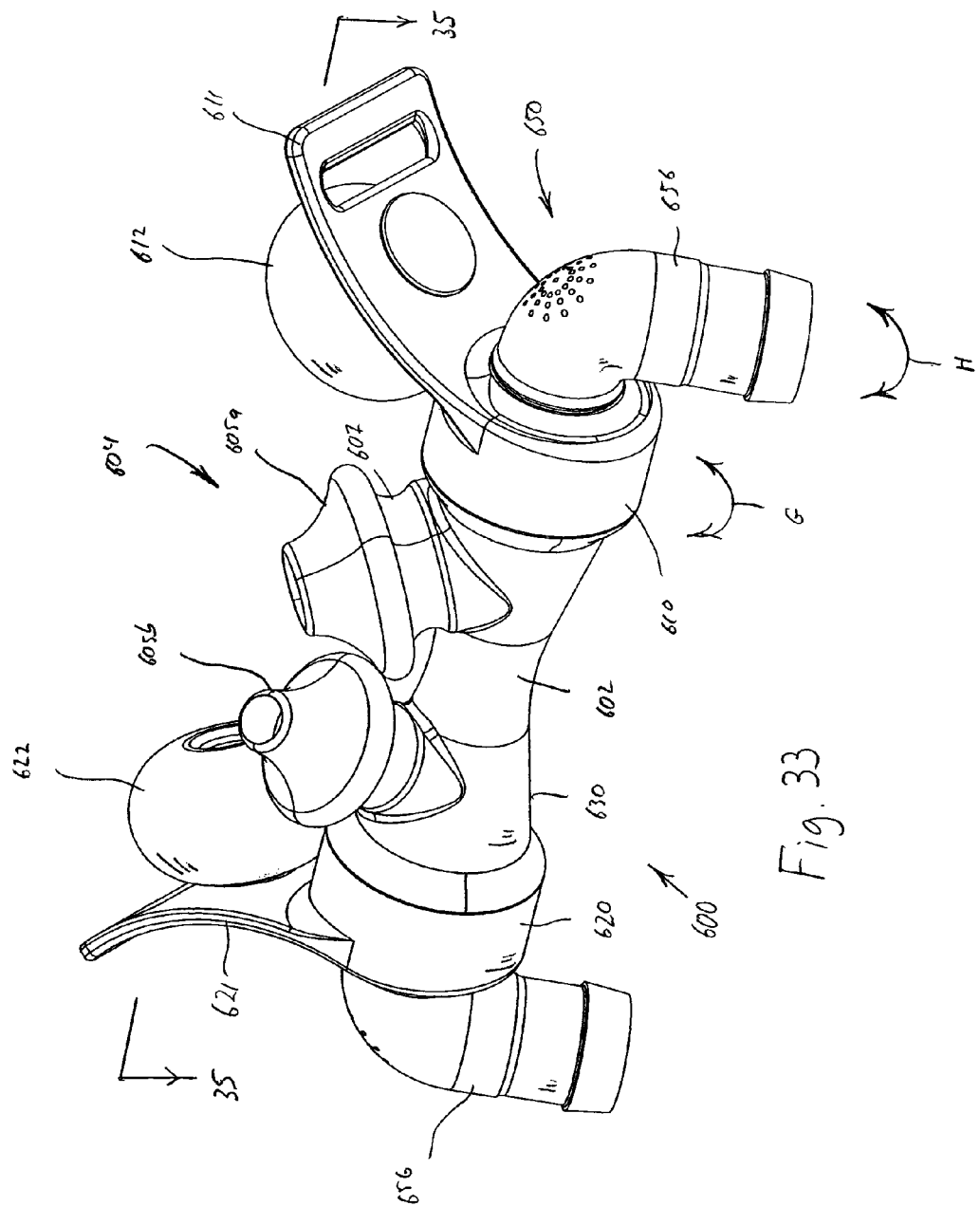
Figure 34:
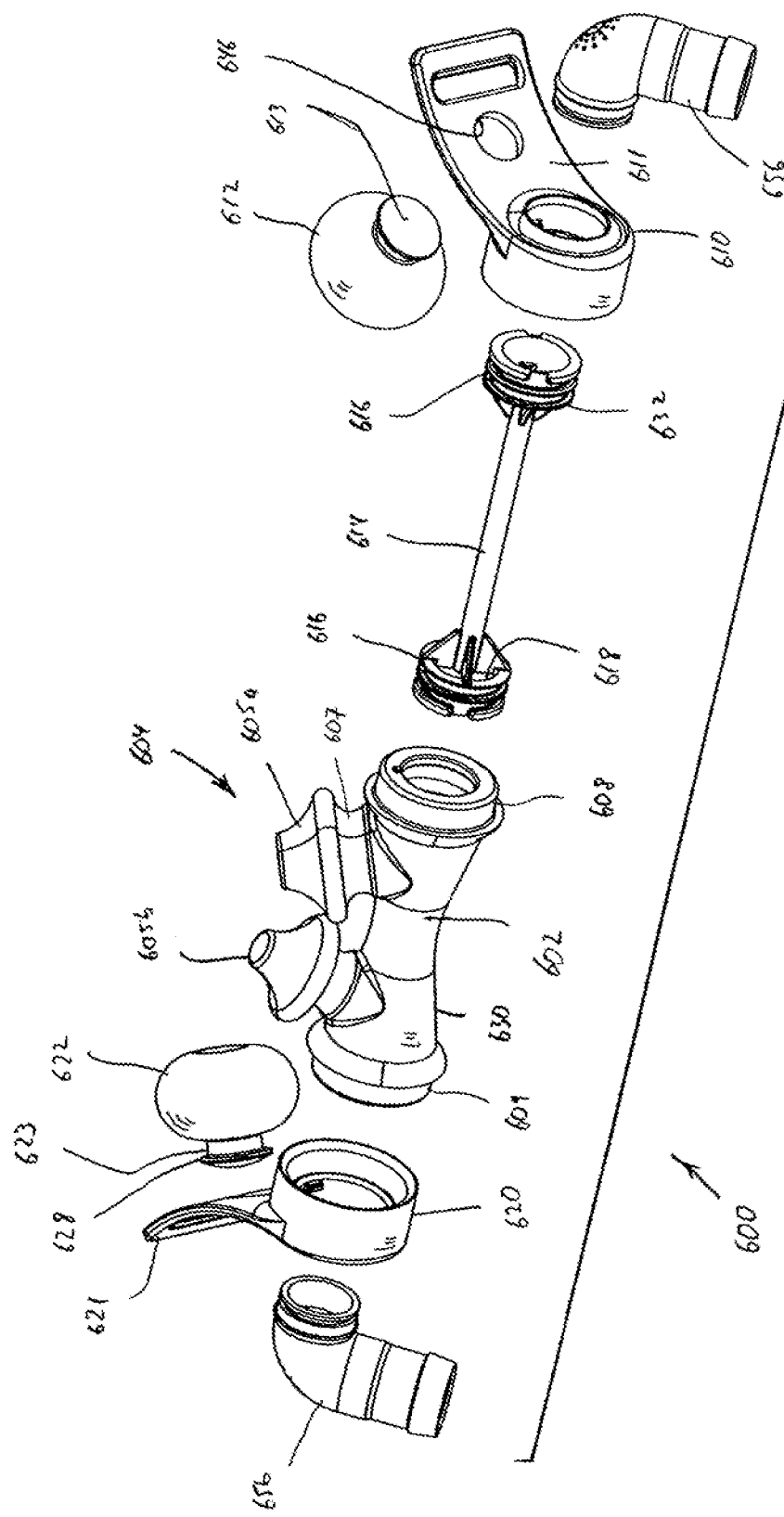
FIG. 34 is an exploded view of the patient interface device of FIG. 32.
Figure 35:
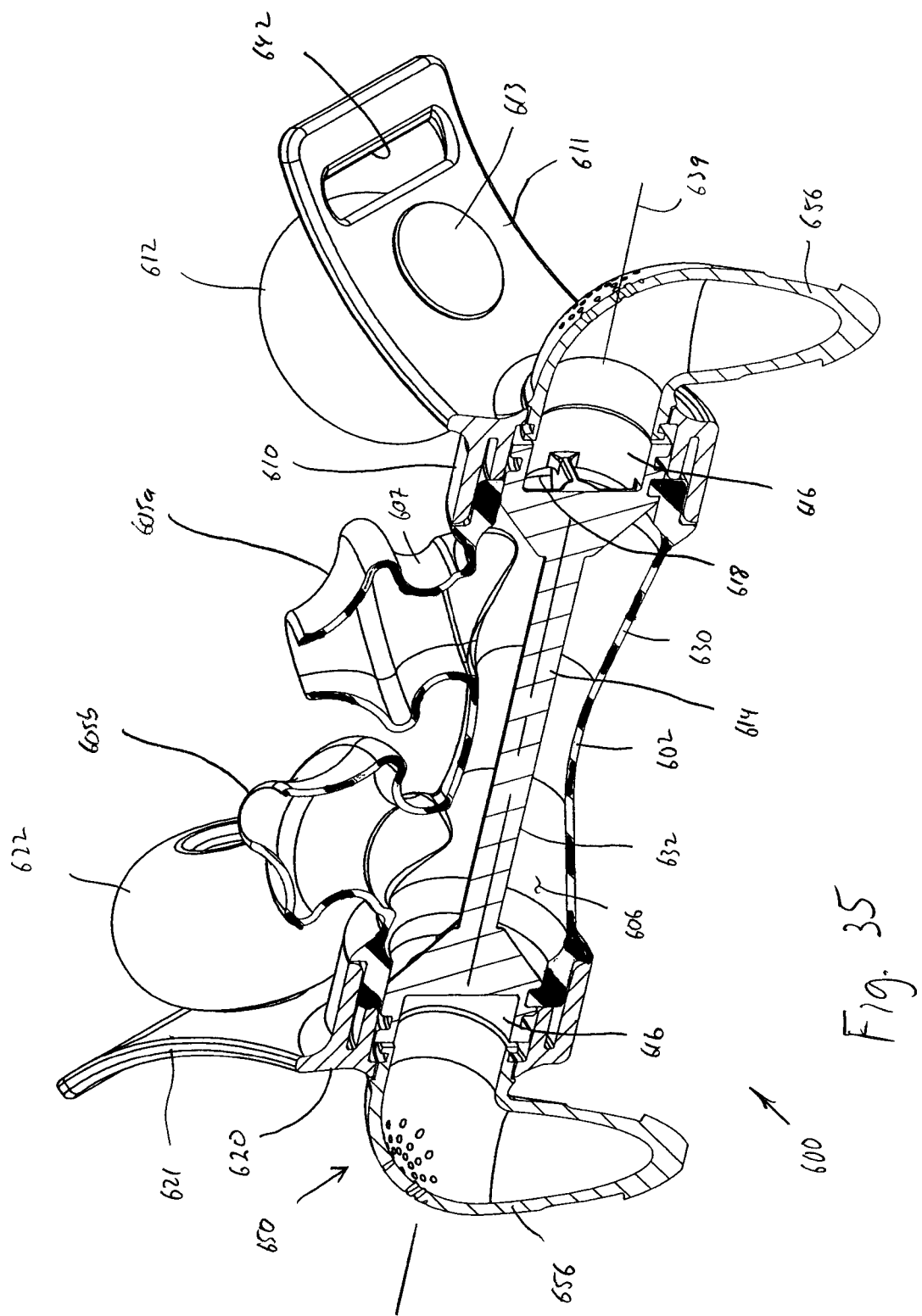
FIG. 35 is a cross-sectional view of the patient interface device of FIG. 32 taken alone line 35-35 of FIG. 33.
Figure 36:
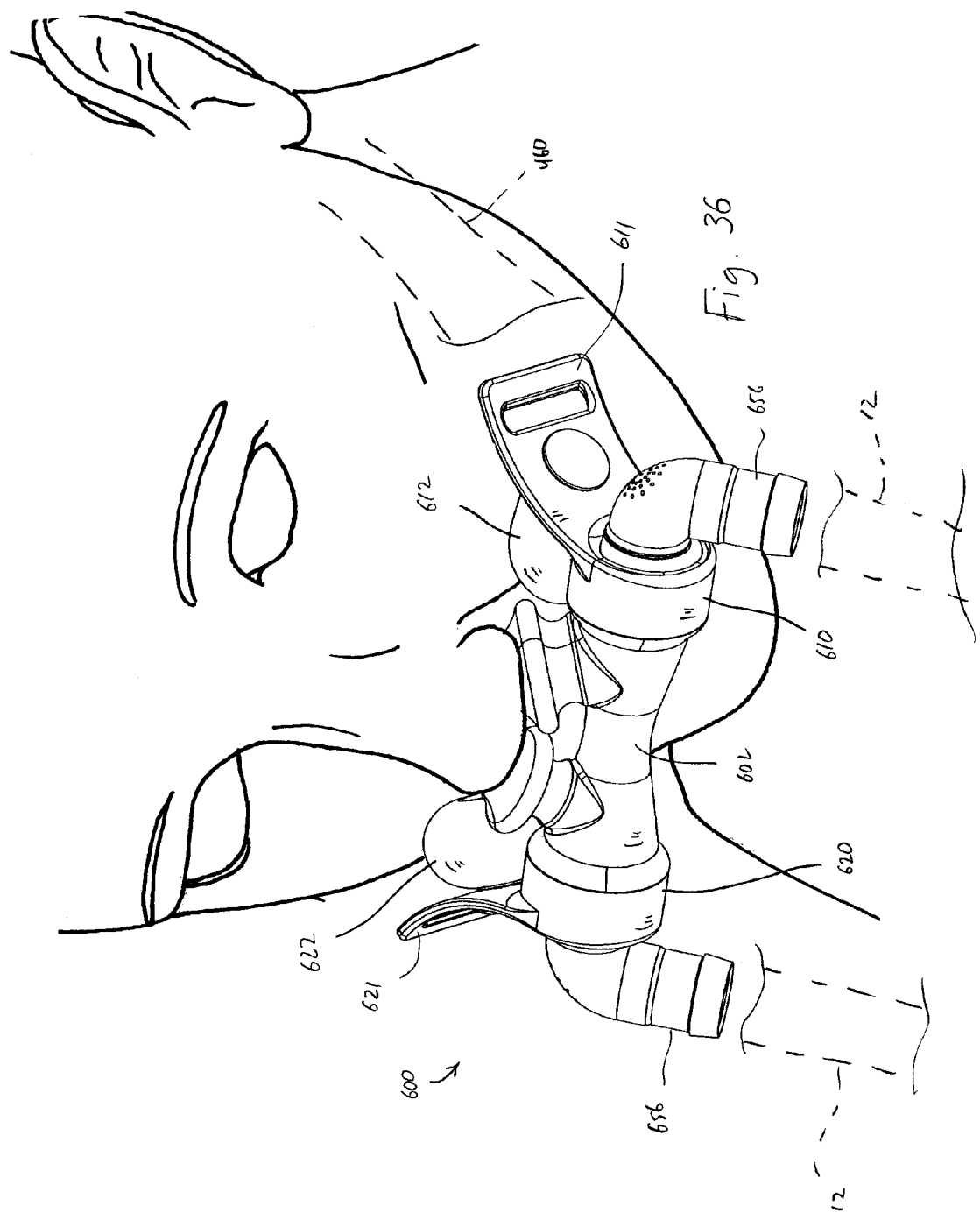
FIG. 36 is a perspective view showing a patient wearing the patient interface device of FIG. 32.

20060231103), the contents of which are incorporated herein by reference. FIG. 29 discussed below also illustrates details of such a coupling structure.

Figure 21:
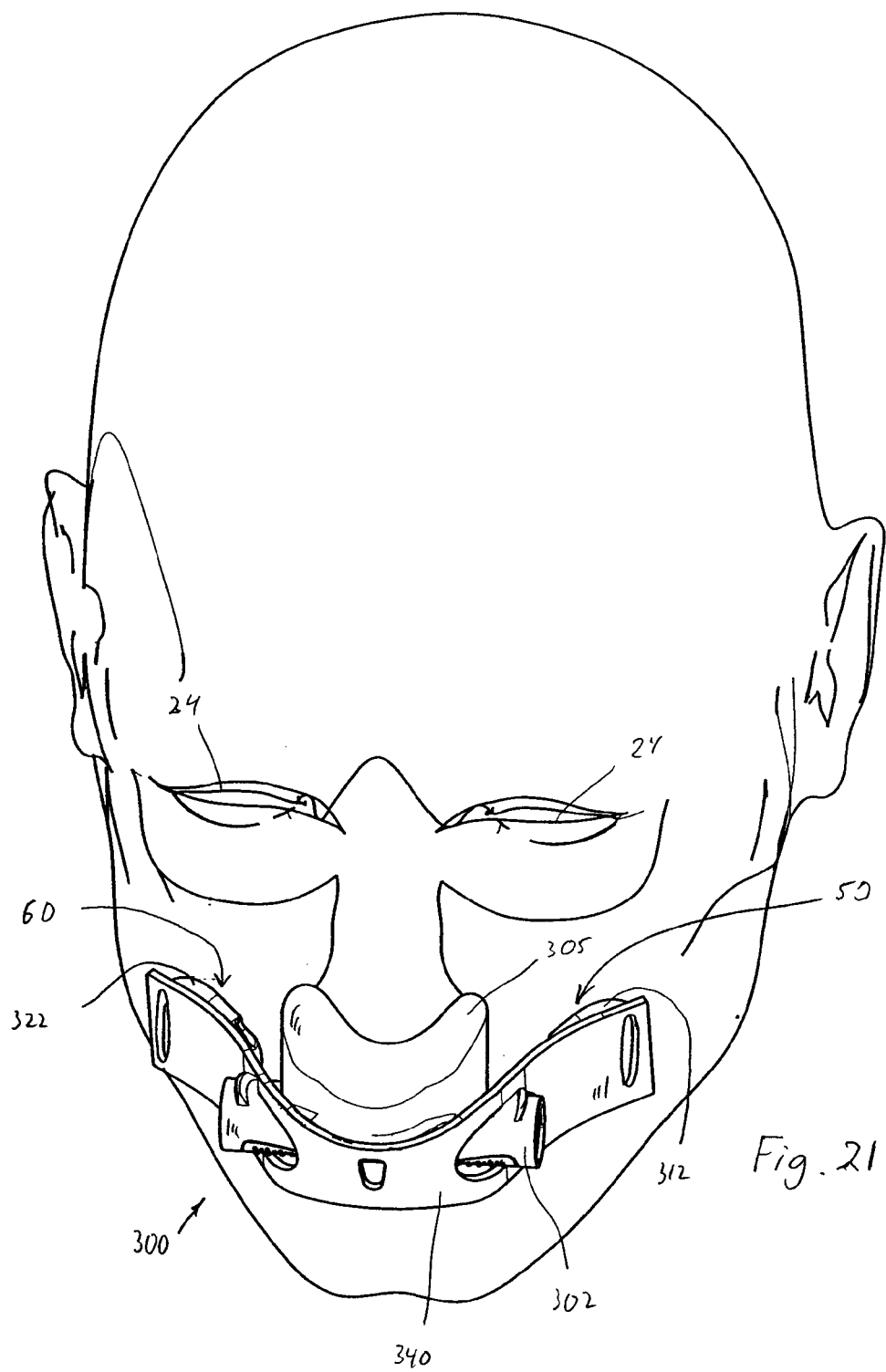
FIG. 21 is a perspective view showing a patient wearing the patient interface device of FIG. 17.
Figure 22:
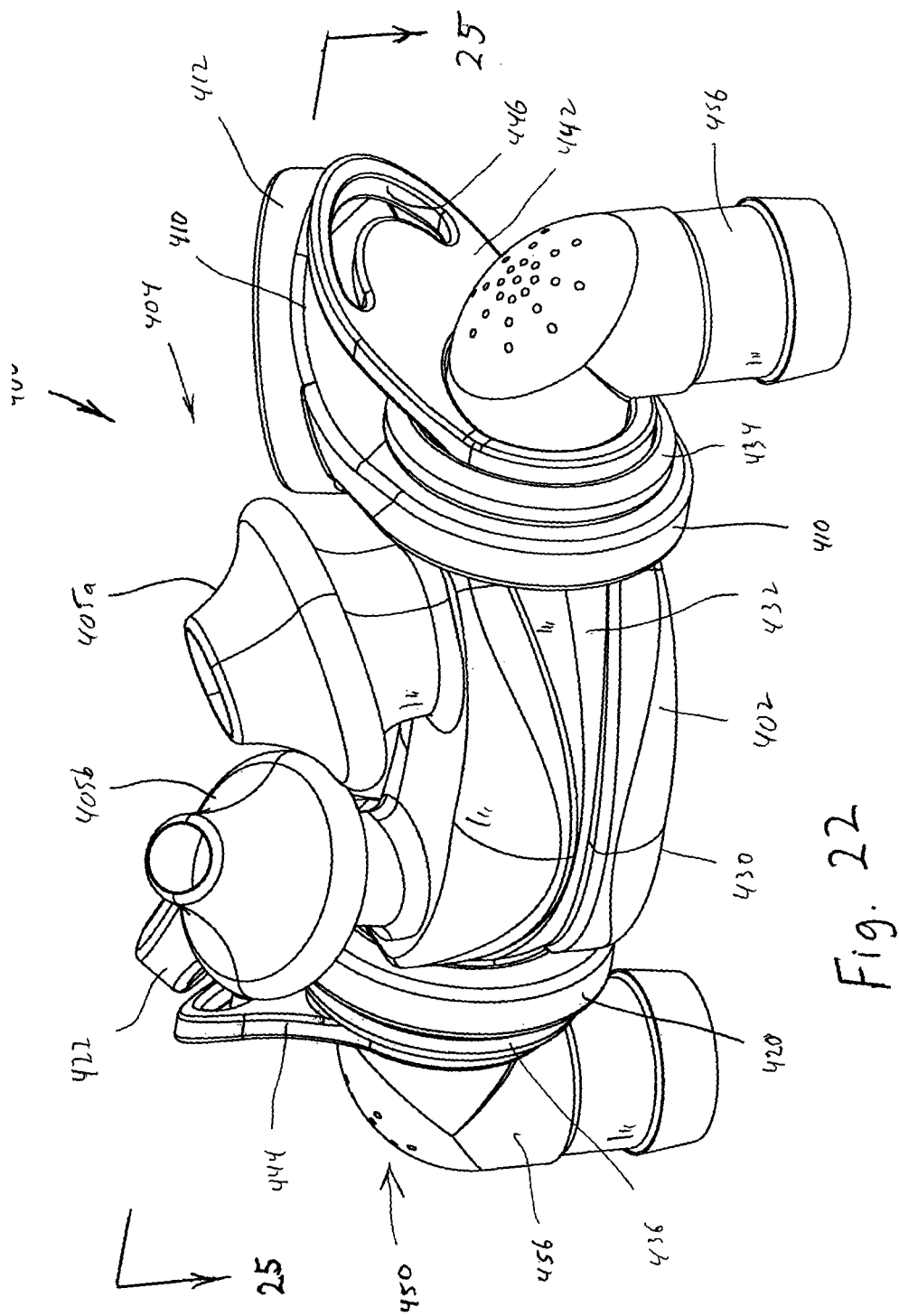
FIGS. 22 and 23 are rear and front perspective views, respectively, of a fourth embodiment of a patient interface device according to the principles of the present invention.
Figure 23:
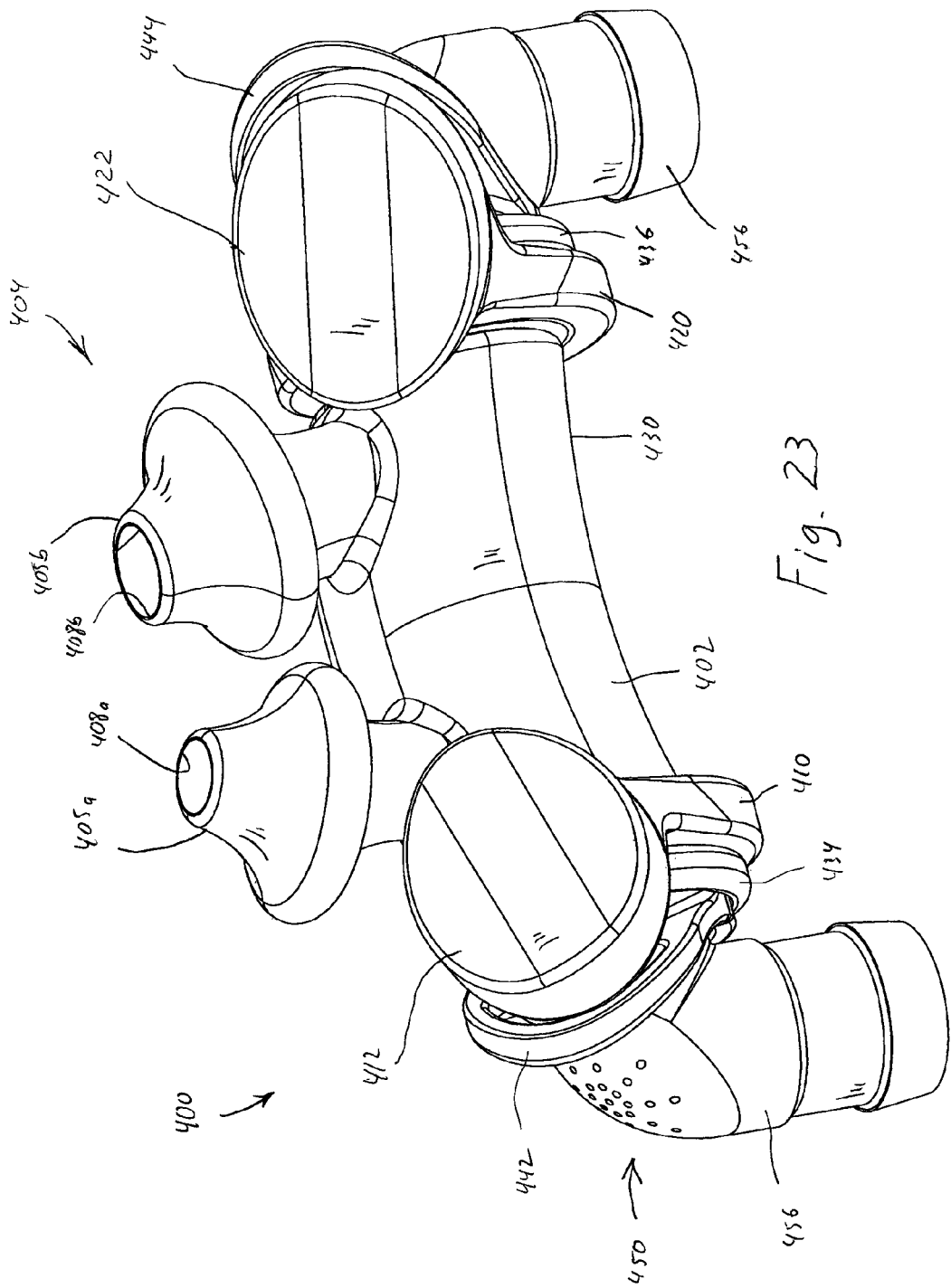

As shown in FIG. 21, when patient interface device 300 is donned by the user, cushion 305 seals around both nares and the remainder of the patient interface device remains below the eyes 24. Pads 312 and 322 overlie only regions 20 and 30, respectively, so that the force imparted against the surface of the face is directed to the regions and is not directed to any other portion of the face.

FIGS. 22-26 illustrate a fourth embodiment of a patient interface device 400 according to the principles of the present invention. Patient interface device 400 includes a support member 402 and a sealing assembly 404 coupled to the support member. Support member 402 includes an internal passage or lumen 406 that serves as a pathway for the flow of gas to and from the user. As in the previous embodiment, one or both ends of support member 402 are coupled to a pressure support system as described in greater detail below.

In an exemplary embodiment, support member 402 includes a semi-rigid or flexible conduit member 430 and a brace member 432, which is generally more rigid that the conduit member. The conduit member and the brace member are coupled together to define the support member. They are coupled together in any suitable fashion such that the brace member remains external or outside of the conduit member. In an exemplary embodiment, conduit member 430 includes a groove that receives brace member 432, fully or partially, when these two components are assembled. Thus, when assembled, the conduit member and the brace member do not move relative to one another, but together they define a unitary component of the patient interface device that support the patient sealing portion, i.e., the portion that sealing against the patient's airway.

Brace member 432 includes a first end portion 434 in the form of a ring and/or flange, a second end portion 436 also in the form of a ring and/or flange, and a strut 438 that extends between the first and second end portions. In an exemplary embodiment, conduit member 430 is formed from a material, such as injection silicone or TPE, which can be the same as the sealing element in a unitary structure, and brace member 432 is formed from a more rigid material, such as polycarbonate, Hytrel, PP, HDPE, or flexible Nylon. Of course the present invention contemplates other configurations, materials, or combinations of materials for the brace member, the conduit member, or portions thereof.

Figure 25:
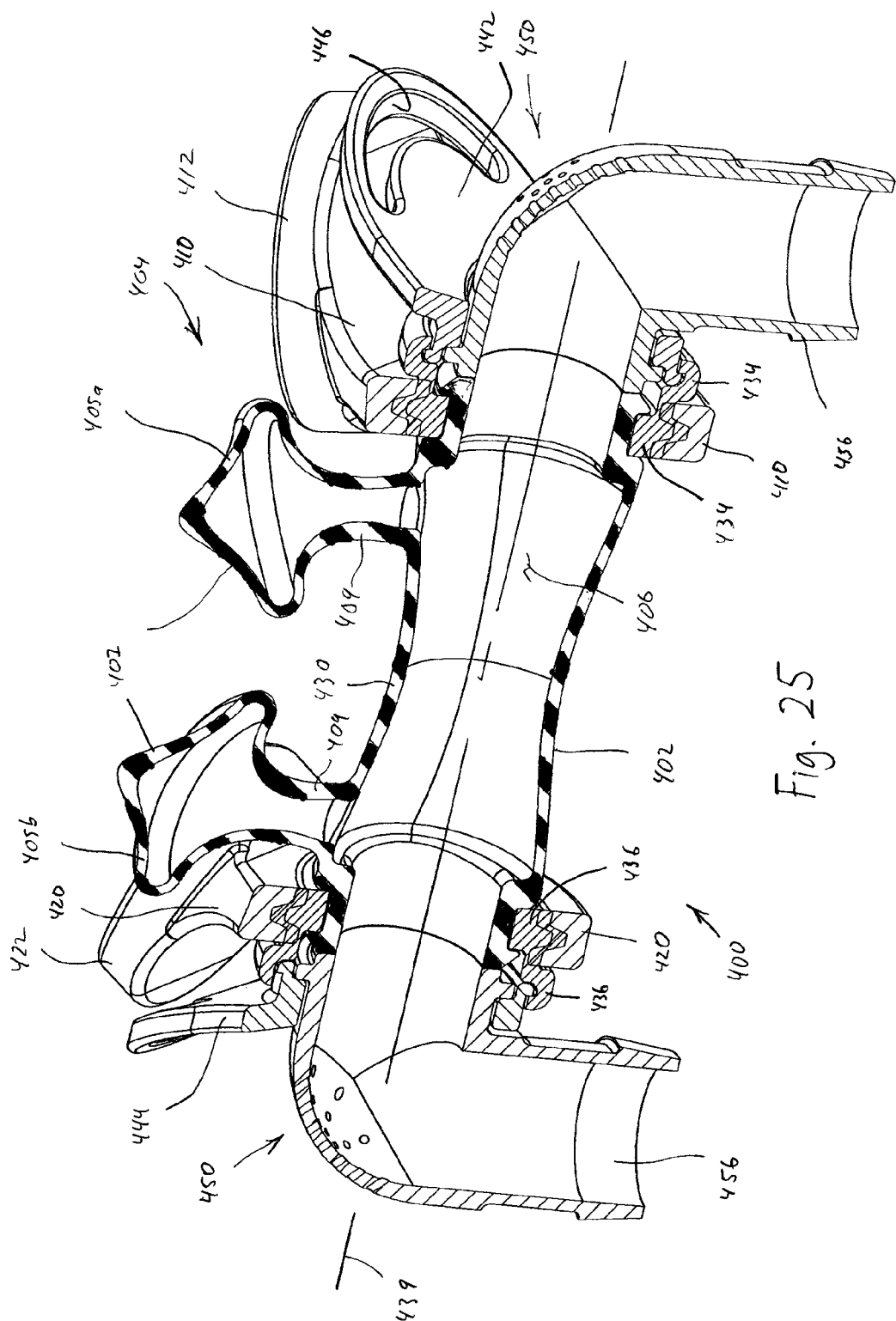
FIG. 25 is a cross-sectional view of the patient interface device of FIG. 22 taken alone line 25-25 of FIG. 22.
Figure 26:
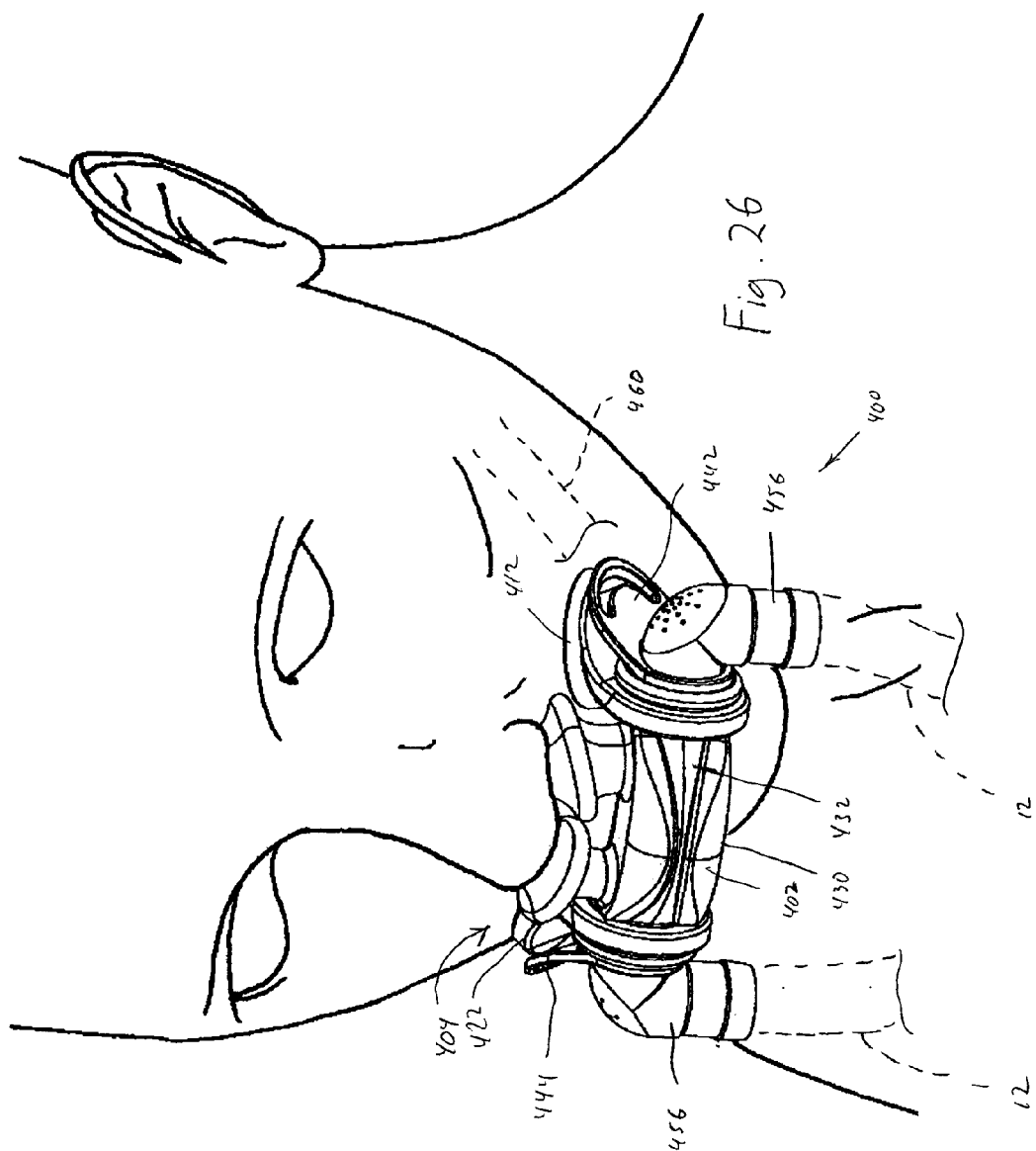
FIG. 26 is a perspective view showing a patient wearing the patient interface device of FIG. 22.
Figure 27:
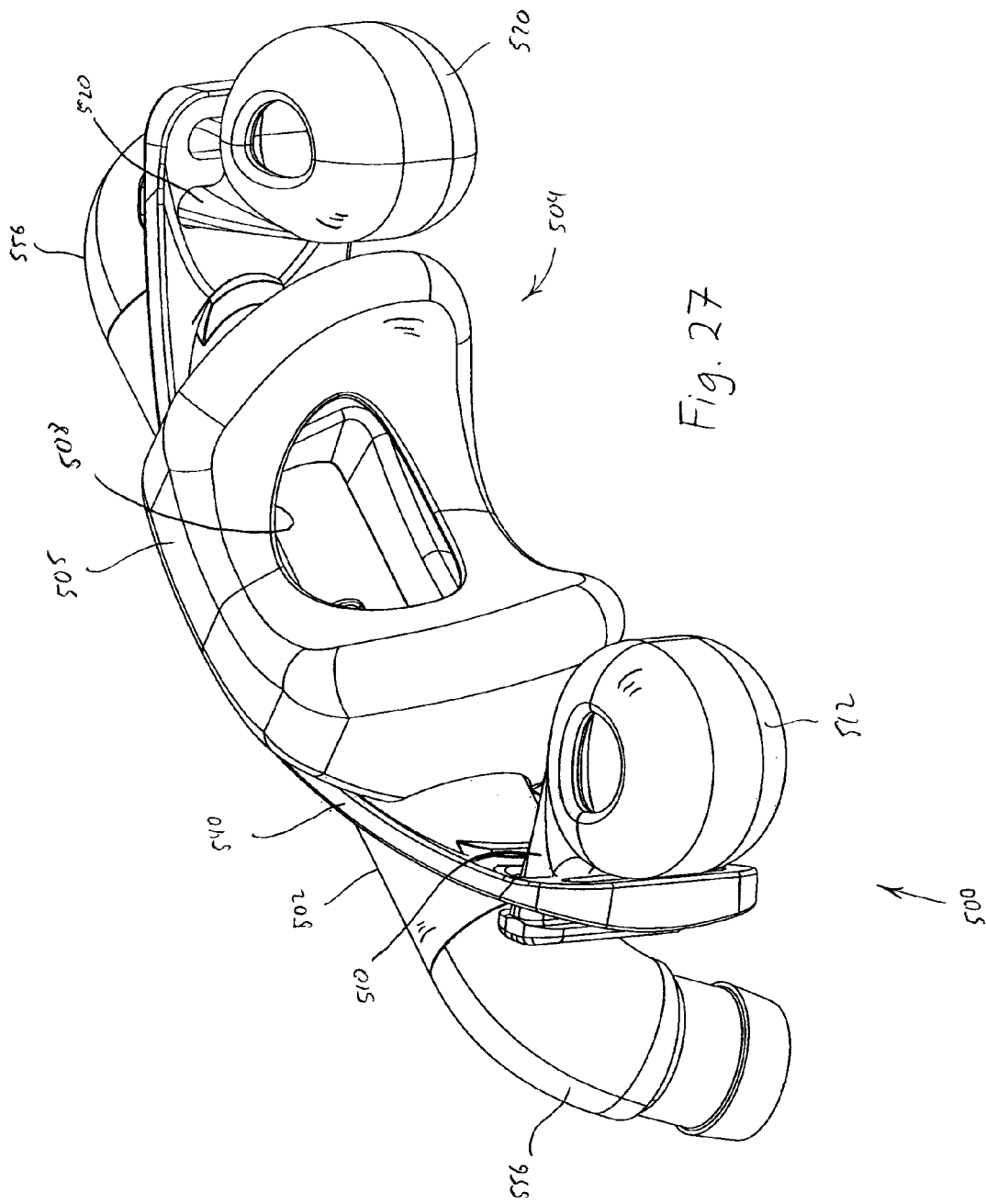
FIGS. 27 and 28 are rear and front perspective views, respectively, of a fifth embodiment of a patient interface device according to the principles of the present invention.
Figure 28:
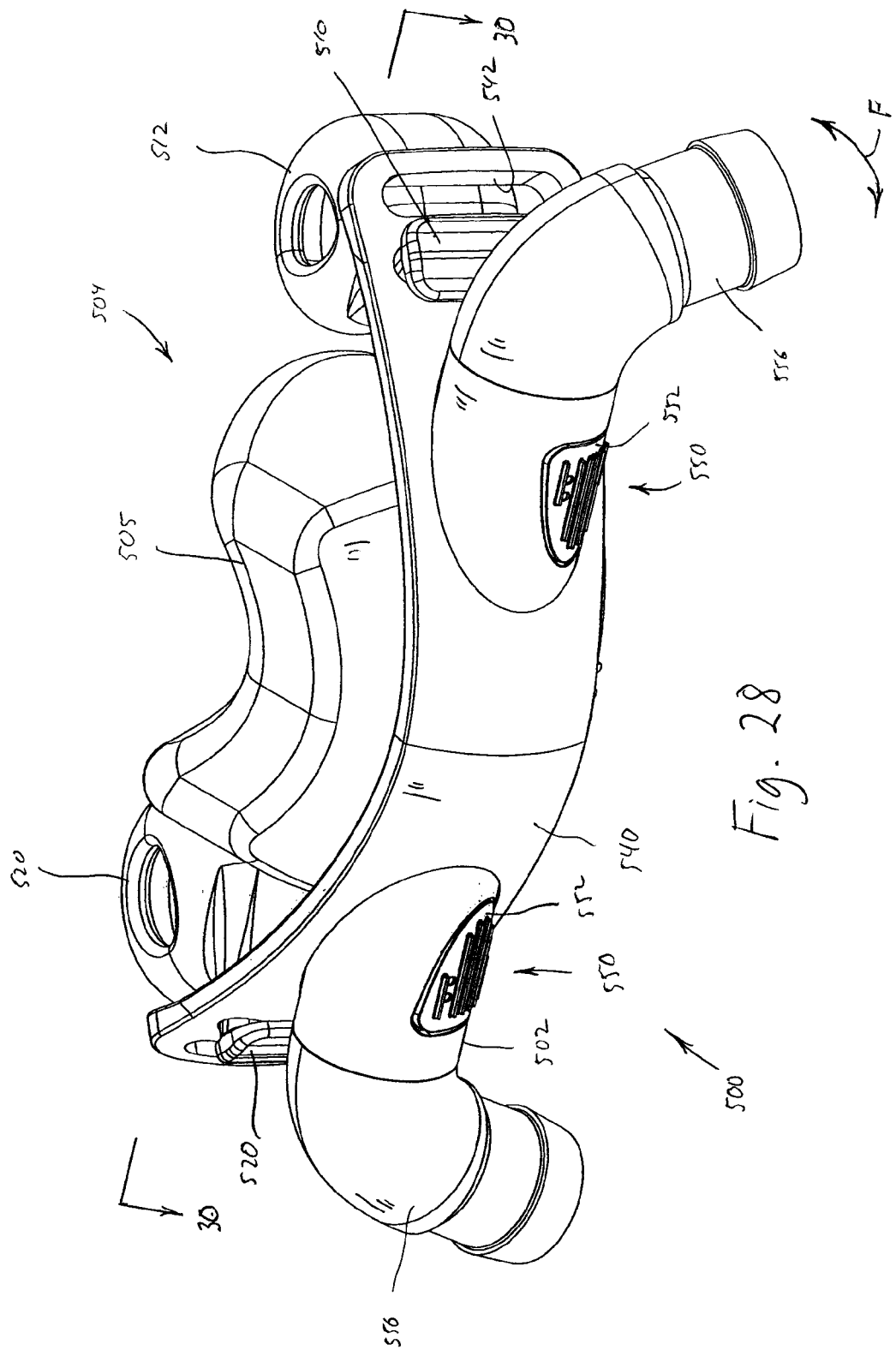

As best shown in FIG. 25, the end portions of conduit member 430 are mounted to first and second end portions 434 and 436 of the brace member by inserting the end portions of the conduit member into the first and second end portions of the brace member. A tongue and groove mechanism retains the brace member coupled to the flexible member. In addition or in the alternative, the conduit member and brace member are sized such that one or both of these members must bend or give, at least slightly, in order to insert the ends of the conduit member into the end portions of the brace member. Once in place, they return to the original position and are maintained in an engaged relation due to their resilient nature.

Sealing assembly 404 is a pair of nasal prongs 405a and 405b each having a "mushroom" configuration. That is, a conical or conical-shaped head 407 is mounted on a stem portion 409 so that gas is communicated from passage 406 to the user through the hollow interior of the nasal prong. Openings 408a and 408b are defined in the head of the nasal prongs to communicate the gas to the user's airway. In the illustrated embodiment, sealing assembly 404 is integral with conduit member 430. It is to be understood, however, that the present invention contemplates that the sealing assembly can be selectively attachable, i.e., separable, from the conduit member so that the nasal prongs can be easily replaced and/or so that other size, shaped, and configured sealing devices can be used as the sealing assembly. For example, the present invention contemplates using a cushion, such as cushion 305 discussed above, as sealing assembly 404.

A first pad 412 is mounted on a first pad support 410 including a first ring portion that is coupled to support member 402. More specifically, in the illustrated exemplary embodiment, first pad support 410 is coupled to first end portion 434 of brace member 432 such that the first pad support rotates relative to the support member 402, as indicated by arrow B in FIG. 24. Similarly, a second pad 422 is mounted on a second pad support 420 including a second ring portion that is coupled to support member 402. More specifically, in the illustrated exemplary embodiment, second pad support 420 is coupled to second end portion 436 of brace member 432 such that the second pad support rotates relative to support member 402. That is, both the first and the second pad supports rotate around a common axis, which a longitudinal axis 439 for the patient interface device. First and second pads 412 and 422 are the contacting members of patient interface device 400 that contact regions 20 and 30 on the face of the user.

In the illustrated embodiment, first and second pads 412 and 422 are generally elliptical or oval shaped with smooth rounded edges. In addition, first and second pad supports 410 and 420 each have an angled arm, where the angle is selected to correspond, generally, the curvature of the average human head. That is, the arms of the pads supports are angled to substantially match the curvature of arc 38. See FIG. 1C. This configuration maximizes patient fit, and, hence, comfort so that the patient interface can be warn for an extended period of time.

It is to be understood, however, that pads 412 and 422, as well as pad supports 410 and 420, can have any one of a variety of configurations, so long as the contacting area on the user is limited to regions 20 and 30 discussed above. In addition, first pad 412 and second pad 422 need not have symmetrical configurations. Likewise, first pad support 410 and second pad support 420 need not have symmetrical configurations.

Pads 412 and 422 can be made from any suitable material, such as gel, foam, silicon, or any combination thereof. In addition, the pads can be permanently attached to first and second pad supports 410 and 420 using any conventional technique, such as an adhesive or mechanical coupling. Conversely, the pads can be removably attached to the pad supports, also using any conventional technique, such as snaps, hook and loop fasteners, or clips. First and second pad supports 410 and 420 can also be made from any suitable material or combination of materials so long as the pad supporting function is achieved. In one embodiment, the pad supports are made from a rigid material. In another embodiment, they are made from a semi-rigid or flexible material so that they can "flex" to optimize patient comfort.

A first headgear support 442 including a third ring portion and a second headgear support 444 including a fourth ring portion are coupled to support member 402. In an exemplary embodiment, the headgear supports are relatively rigid members that are rotatably attached to the support member so that they two can be rotated about axis 439, as indicated by arrow C in FIG. 24. More specifically, a ring portion of first headgear support 442 connects to first end portion 434 of support member 402 using a tongue and groove configuration. Of course, the technique for connecting the headgear supports to the support member is not limited to that shown. Other techniques are contemplated including merely reversing the tongue and groove orientations.

Headgear supports 442 and 444 include arms 452 and 454, respectively, each of which extends away from axis 439 at an non-90° angle with respect to that axis. In an exemplary embodiment, the angle of arms 452 and 454 is selected to that the headgear straps remains generally parallel to the surface of the user when the patient interface device and headgear assembly are donned by the user. The present invention also contemplates forming one or both arms 452 and 454 from a flexible or semi-rigid material so that they and flex to allow the headgear strap to align itself relative to the patient and/or the patient interface device as the straps are tightened.

A portion of a headgear assembly, such as a strap (shown in phantom lines 450 in FIG. 26), attaches to first headgear support 442 and second headgear support 444 in any suitable fashion so that patient interface device 400 can be held on the user. In the illustrated exemplary embodiment, first headgear support 442 includes a first slot 446 and second headgear support 444 includes a second slot 448. The headgear straps insert into the slots and the free end is coupled back to the strap using any suitable configuration, such as a snap or hook and loop connector. Of course, any technique for connecting the headgear to the headgear supports are contemplated by the present invention.

Conduit coupling 456 are provided at a first end of support member 402 and at a second end of the support member opposite the first end. Conduit couplings 456 couple patient circuit 12 to each end of the patient interface device. In the illustrated embodiment, the conduit couplings are connected to support member 402 or to headgear supports 442 and 444, which are connected to the support member. In a still further embodiment, conduit couplings 456 are connected to the support member such that they are rotatable relative to the support member, as indicated by arrow D, in FIG. 24.

In the illustrated embodiment, conduit couplings 456 are angled to redirect the gas carrying conduits in a desired direction. While the conduit couplings are shown as having a generally 90° angle, any angle suitable angle is contemplated by the present invention, including a 0° angle. In an exemplary embodiment of the present invention, conduit couplings 456 are formed from a rigid material. However, the present invention also contemplates the conduit couplings can be formed from a flexible or semi-rigid material, or a combination of materials.

Exhaust assemblies 450 are provided on conduit couplings 456. As with the exhaust assemblies of the previous embodiments, exhaust assemblies 450 are provided to vent gas from the interior of the patient interface device to ambient atmosphere. The present invention contemplates that exhaust assemblies 450 can have any configuration, so long as the function of exhausting a sufficient amount of gas to atmosphere is achieved. In the illustrated embodiment, exhaust assemblies 450 are defined by a plurality of vent holes provided in the wall of conduit couplings 456. The present invention contemplates that the pattern of the holes, size of each hole, number of holes, and the location of the holes, can be changed from that shown, including providing the holes on other components of the patient interface device.

From the above description, it can be appreciated that by allowing pad supports 410 and 420, headgear supports 442 and 444, conduit couplings 456 or any combination thereof to rotate, patient interface device 400 can be adjusted to fit a wide variety of different patients. In an exemplary embodiment, the rotation of one or more components is a continuous, i.e., non-discrete, so that each component can move over a wide range of dimensions. This makes it possible for each of these rotatable components to "self-align" on the user. That it, when the patient interface device is donned by they user, each component that is allowed to rotate will seeks its natural position. Thereby providing a high degree of flexibility in fitting a commonly sized patient interface device on a wide variety of users.

In a further embodiment, one or more of the rotatable components are rotatable over a discrete number of positions in a ratchet-like fashion. This enables the user to select the desired position of each component and maintain the patient interface device in the selected position.

Figure 24:
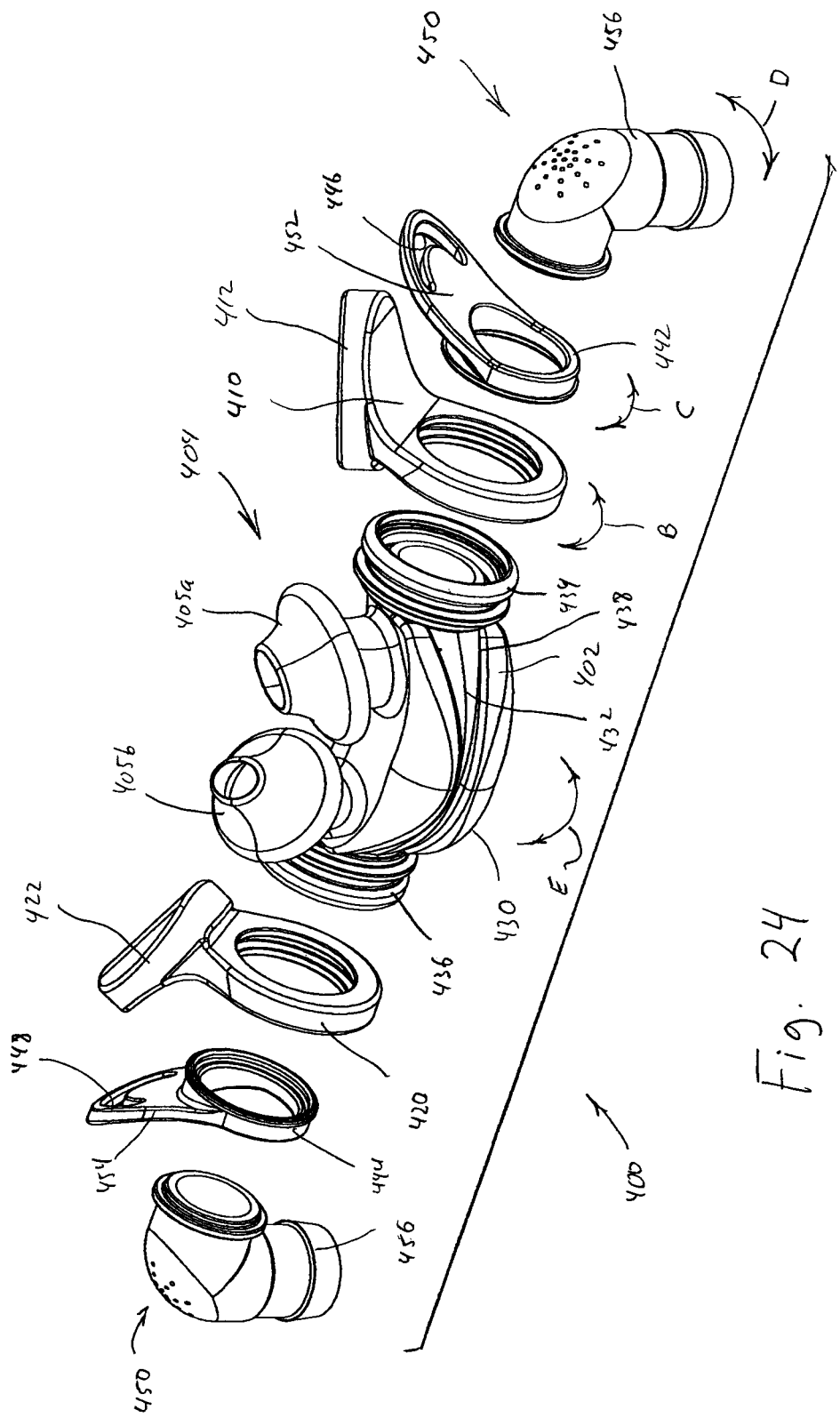
FIG. 24 is an exploded view of the patient interface device of FIG. 22.

Because of the rotatable relation between the various components, it is possible to move support member 402 in a rotatable fashion relative to the other components, as indicated by arrow E in FIG. 24. It is to be further understood that other features and elements can be use with patient interface device. For example, alignment indicators can be provided on one or more of the rotating components to indicate the angular position of one component relative to another component.

FIGS. 27-31 illustrate a fifth embodiment of a patient interface device 500 according to the principles of the present invention. Patient interface device 500 includes a support member 502 and a sealing assembly 504 coupled to the support member. In the illustrated exemplary embodiment, support member 502 is a relatively rigid or semi-rigid tube having an internal passage or lumen 506 defined therein that serves as a pathway for the flow of gas to and from the user. As in the previous embodiments, one or both ends of support member 502 are coupled to a pressure support system as described in greater detail below. In addition, an opening 507 is provided in support member 502 to communicate gas to and from sealing assembly 504.

Exhaust assemblies 550 are provide at each end of the support member. As shown in detail in FIG. 29, the exhaust assemblies are formed by securing an exhaust plate 552 over an opening 554 in the support member. This allows for flexibility in the selection of the characteristics of the exhaust assembly merely by securing different exhaust plates to the support member.

Sealing assembly 504, in this illustrated exemplary embodiment, is a single cushion 505, which is similar, if not identical, to support cushion 305 discussed above. Cushion 505 is sized and configured to seal around the nares of the user and includes a single opening 508 to communicate the user's airway with passage 506 in support member 502. Cushion 505 is attached to support member 502 in any conventional technique. However, in the illustrated embodiment, the cushion is attached to the support member by means of a coupling structure 518 provided in or coupled to cushion 505. Coupling structure 518 corresponds to coupling structure 318 discussed above, and is a rigid or semi-rigid member that is embedded in the material forming the cushion. A portion or portions of the coupling structure, such as tabs 524, extend from the cushion to engage a groove or grooves provided in the support member.

The coupling structure and the cushion are coupled to one another in any conventional manner. However, in an exemplary embodiment, the cushion is molded over the coupling structure. To ensure a secure attachment of the cushion to coupling structure 518, a plurality of openings 526 are formed in the coupling structure so that the material defining the cushion can flow into these openings.

Patient interface device 500 includes a support frame 540 that has a generally curved shape. The radius of curvature for the support frame is selected to generally match the radius of arc 38 discussed above. Support frame 540 is made from any suitable material or combination of materials. However, in an exemplary embodiment, support frame 540 is formed from a semi-rigid material so that the support frame can flex to increase or decrease its radius of curvature to suit the particular facial features of the user. Support frame 540 includes headgear attachment slots 542 to receive headgear strap 460. In the illustrated embodiment, support frame and is coupled to support member 502 as discussed above with respect to support frames 140, 240, and 340.

A first pad 512 is coupled to support frame 540 via a pad support 510, and a second pad 522 is coupled to an opposite end of the support frame via a pad support 520. In this exemplary embodiment, pads 512 and 522 are formed from a flexible material, such as silicone, and have a cylindrical or barrel shape with one more hollow chambers defined therein. This allows the pads to give or compress while also increasing the contact area, and hence the distribution of the load as the user tightens the mask on his or her face. In this embodiment, pad supports 510 and 520 are unitarily formed with the associated pad. Thus, the pad and pad support are a single piece, as best shown in FIG. 29. Of course, the present invention contemplates that the pads and pad supports can be formed from separate components and attached together in any suitable manner, either permanently or separably.

Pad supports 510 and 520 are coupled to support frame 540 by inserting a portion of the pad support into a pad support slot 546 defined in the support frame. The pad support include a flexible flange 528 that compresses to allow the pad supports to insert into the pad support slots and rebounds back to substantially their original shape to prevent the pad supports from readily pulling out of the pad support slots. The pad supports are removed from the support frame simply by pulling on them with sufficient force to cause the flange to deflect thereby releasing the pad support from slot 546. The shape, size, and configuration of pad supports 510 and 520, flange 528, and slots 546 can be varied. In addition, the present invention contemplates providing multiple pad support slots on the support frame so that the user can select the appropriate slot that allows the pads to be positioned on regions 20 and 30 discussed above. Also, other techniques for attaching the pad supports to the support frame, permanently or removable, are contemplated by the present invention.

Conduit couplings 556 are provided at each end of support member 502 to couple patient circuit 12 to each end the patient interface device. In the illustrated embodiment, the conduit couplings are connected to support member 502 such that they rotate relative to the support member, as indicated by arrow F, in FIG. 28. This allows the position of the patient circuit to be adjusted and prevent or minimizes movement of the patient circuit from imparting a torque on the patient interface device. Such torque is known to dislodge or degrade the seal provided by the sealing assembly.

FIGS. 32-36 illustrate a sixth embodiment of a patient interface device 600 according to the principles of the present invention. Patient interface device 600 includes a support member 602 and a sealing assembly 604 coupled to the support member. In the illustrated exemplary embodiment, support member 602 includes a flexible or semi-rigid conduit member 630 and a relatively rigid or semi-rigid brace member 632. An internal passage or lumen 606 is defined in the conduit member that serves as a pathway for the flow of gas to and from the user. As in the previous embodiments, one or both ends of support member 602 are coupled to a pressure support system.

Unlike the other embodiments, in this embodiment, brace member 632 is provided within conduit member 630 such that the brace member, or portions thereof, are disposed in passage 606. The brace member includes a central bar or rod 614 and end portions 616. The end portions of the brace member are coupled to end portions of conduit member 630, for example, by means of a friction fit. Thus, the brace member and the conduit member form a unitary component with the brace member providing the structural support for the support member and the conduit member forming the gas carrying conduit. Openings 618 are provided in end portions 616 so that gas from the patient circuit can flow to and from passage 606. It is to be understood that the brace member and the conduit member can have configurations other than those shown.

Sealing assembly 604 is a pair of nasal prongs 605a and 605b each having a "mushroom" configuration and a stem 607 that is integrally formed with conduit member 630. It is to be understood, however, that the present invention contemplates that the sealing assembly can be selectively attachable, i.e., separable, from the conduit member so that the nasal prongs can be easily replaced and/or other size, shaped and configured sealing devices can be used in combination as the sealing assembly. The present invention contemplates using a cushion, such as cushion 305 or 505 discussed above, as sealing assembly 604. The cushion can be integral, separably, or permanently joined to conduit member 630.

A first pad support 610 is coupled to a first end portion 608 of support member 602, and a second pad support 620 is coupled to a second end portion 609 of the support member. More specifically, in the illustrated embodiment, as perhaps best shown in FIG. 35, the first and second pad supports are coupled to end portions of conduit member 630 and end portions of brace member 632. Of course, the present invention contemplates that the pad supports need only be coupled, directly or indirectly, to one of these components of the support member. The first and second pad supports are either rotatably coupled to the ends of the support member or fixed to the ends thereof using any suitable technique. When rotatably coupled, the first and second pads supports rotate around a longitudinal axis 639 of the patient interface device, as indicated by arrow G in FIG. 33.

Pad supports 610 and 620 each include an arm 611 and 621, respectively, that extends at an angle away from the portion of the pad support that is joined to the support member. This angle of each arm is selected to correspond, generally, the curvature of the average human head, i.e., arc 38 of FIG. 1C. The pad supports, arms, or both are formed from any suitable material. For example, the present invention contemplates forming arms 611 and 621 such that they can flex or bend, at least slightly. Pad supports 610 and 620 each include at least one headgear attachment slots 642 to receive headgear strap 460.

A first pad 612 is coupled to first pad support 610, and a second pad 622 is coupled to second pad support 620. In this exemplary embodiment, pads 612 and 622 are formed from a flexible material, such as silicone, gel or foam or a combination of materials, and have a circular or elliptical shape with one or more hollow chambers defined therein. This allows the pads to give or compress while also increasing the contact area, and hence the distribution of the load as the user tightens the mask on his or her face.

Pads 612 and 622 include an attachment portion, 613 and 623, respectively, to selectively attach the pad to the associated pad support. More specifically, pads 612 and 622 are coupled to pad supports 610 and 620 by inserting at least a portion of the attachment portion into a pad support slot 646 defined in pad supports 610 and 620. Attachment portions 613 and 623 include a flexible flange 628 that compresses to allow the pad to insert into the pad support slots and rebounds back to substantially their original shape to prevent the pad from readily pulling out of the pad support slots. The pads are removed from the support frame simply by pulling on them with sufficient force to cause the flange to deflect thereby releasing the pad support from slot 646.

The shape, size, and configuration of pad supports 610 and 620, attachment portions 613 and 623, flange 628, and slots 646 can be varied. In addition, the present invention contemplates providing multiple pad support slots on the pad supports so that the user can select the appropriate slot that allows the pads to be positioned on regions 20 and 30 discussed above. Also, other techniques for attaching the pad supports to the support frame, permanently or removably, are contemplated by the present invention.

Conduit couplings 656 are provided at a first end of support member 602 and at a second end of the support member opposite the first end. Conduit couplings 656 couple patient circuit 12 to each end the patient interface device. In the illustrated embodiment, the conduit couplings are connected to support member 602 or to pad supports 610 and 620, which are connected to the support member. In a still further embodiment, conduit couplings 656 are connected to the support member such that they are rotatable relative to the support member, as indicated by arrow H, in FIG. 33.

Exhaust assemblies 650 are provided on conduit couplings 656. As with the exhaust assemblies of the previous embodiments, exhaust assemblies 650 are provided to vent gas from the interior of the patient interface device to ambient atmosphere and can have any configuration, so long as the function of exhausting a sufficient amount of gas to atmosphere is achieved. In the illustrated embodiment, exhaust assemblies 650 are defined by a plurality of vent holes provided in the wall of conduit couplings 656. The present invention contemplates that the pattern of the holes, size of each hole, number of holes, and the location of the holes, can be changed from that shown, including providing the holes on other components of the patient interface device.

FIGS. 37 and 38 are front and rear perspective views, respectively, of a seventh embodiment of a patient interface device 700 according to the principles of the present invention. Patient interface device 700 includes a support member 702 and a sealing assembly 704 coupled to the support member. This embodiment is provided to show that the sealing assembly can have still other configurations.

In this illustrated exemplary embodiment, sealing assembly 704 is a full face mask that seals both the nose and mouth of the user. The sealing assembly includes a faceplate 760 that is coupled to support member 702. An opening 708 in the support member communicates the interior of the support member with a chamber defined by the faceplate. A cushion 762 or sealing element is coupled to the faceplate to form a seal with the surface of the user. Faceplate 760 and cushion 762 can have configuration so long as they accomplish the function of sealing the patient airway in a leak resistant manner. For example, cushion 762 can have multiple flaps at the distal end, which the end closest to the surface of the patient. Cushion 762 can have a balloon configuration and can include pleats or gussets at one or more locations.

The present invention also contemplates that the sealing assembly seals only the nares, as in the previous embodiment, but covers at portion of the nose, such as the bridge of the nose. In addition, the faceplate can be eliminated entirely so long as the cushion is structurally strong enough to seal effectively with the surface of the user.

As in the previous embodiments, patient interface device 700 includes pads 712 and 722 coupled to a support frame 740, which itself is coupled to support member 702. Headgear straps 460 attach to the support frame. Conduit couplings 756 are provided at one or both ends of support member 702, either in a rotating or a fixed relation to couple patient circuit 12 to the support member.

The present invention contemplates that the patient interface device of the present invention can include other features. For example, a port, typically for pressure or temperature monitoring or oxygen delivery, can be provided in any portion in the patient interface device. In addition, the patient contacting portions can be made from any suitable material or combination of materials that function for the intended purpose. Any rotatable coupling between two components of the patient interface device can have a continuous range of settings or a discrete range of setting. The present invention also contemplates that any headgear assembly can be used with the patient interface device.

It can also be observed from the foregoing description of the invention that if the support member is relatively strait and the pads are coupled to the support member, as is the case in FIGS. 5-26 and 32-36, the pad support elements are angled to match the curvature of the human face, i.e., arc 38, so that the pads are properly positioned or oriented relative to the surface of the user. If, on the other hand, the support member is relatively strait, but the pads are connected to a curved or curvable support, as is the case in FIGS. 27-31, 37 and 38, the pad support elements that couple need not be angled, but can directly connect the pads to the curved support element.

The present invention also contemplates that the patient interface device of can include additional support structures that contact other portions of the head of the user, so long as the other portions are above the eyes, below the mouth, or both. For example the patient interface device or a patient interface assembly using the patient interface device of the present invention can include a forehead support, a chin support, or both. An example of a suitable forehead support is disclosed in U.S. patent application Ser. No. 10/654,379 (publication no. 20040045551), the contents of which are incorporated herein by reference. An example of a suitable chin support is disclosed in U.S. patent application Ser. No. 11/048,680 (publication no. 20050205096), the contents of which are incorporated herein by reference. An example, of a combined forehead and chin support is disclosed in U.S. patent application Ser. No. 10/953,642 (publication no. 20050072428), the contents of which are incorporated herein by reference. It should be emphasized that regions 20 and 30, which are the area of limited support, are located in an area of the face that is below the eyes and above the mouth. That is, as to the area of the face above the mouth and below the eyes, the patient interface device of the present invention contacts the user for support purposes only in regions 20 and 30.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:
1. A patient interface device comprising:
a support member;

a sealing assembly operatively coupled to the support member, wherein the sealing assembly is adapted to contact a user and communicate a flow of gas to an airway of the user;

a first support frame operatively coupled to a first end portion of the support member, the first support frame having a first right portion provided around an outer surface of the first end portion;

a second support frame operatively coupled to a second end portion of the support member opposite the first end portion, the second support frame having a second ring portion provided around an outer surface of the second end portion, wherein the first support frame is separate from the second support frame;

a first contacting member operatively coupled to the first support frame;

a second contacting member operatively coupled to the second support frame;

a first headgear support operatively coupled to the first end portion of the support member, the first headgear support having a third ring portion received within the first end portion of the support member; and a second headgear support operatively coupled to the second end portion of the support member, the second headgear support having a fourth ring portion received within the second end portion of the support member; wherein the first support frame and the second support frame are flexible or semi-rigid, wherein the first contacting member and the second contacting member are each configured and arranged to contact the user over a limited contacting region, and wherein the limited contacting region corresponds to a junction of the orbicularis oris facial muscle, the zygomaticus facial muscle, and the risorius facial muscle.

2. The patient interface device of claim 1, wherein the sealing assembly comprises a pair of prongs, a cushion, or a cushion and a faceplate.

3. The patient interface device of claim 1, further comprising an angled conduit member having a first end received within the third ring member of the first headgear support and a second end adapted to be coupled to a source of the flow of gas.

4. The patient interface device of claim 1, further comprising
a headgear assembly operatively coupled to the first headgear support and the second headgear support.

5. The patient interface device of claim 1, wherein the sealing assembly is rotatable relative to the first contacting member and the second contacting member.

6. The patient interface device of claim 1, wherein the support member and the sealing assembly are coupled together to define a gas flow path.

7. A patient interface device comprising:
a support member;
a sealing assembly operatively coupled to the support member, wherein the sealing assembly is adapted to contact a user and communicate a flow of gas to an airway of the user;

a first support frame operatively coupled to a first end portion of the support member, the first support member having a first ring portion provided around an outer surface of the first end portion;

a second support frame operatively coupled to a second end portion of the support member opposite the first end portion, the second support frame having a second ring portion provided around an outer surface of the second end portion, wherein the first support frame is separate from the second support frame;

a first contacting member operatively coupled to the first support frame;

a second contacting member operatively coupled to the second support frame;

a first headgear support operatively coupled to the first end portion of the support member, the first headgear support having a third ring portion received within the first end portion of the support member; and a second headgear support operatively coupled to the second end portion of the support member, the second headgear support having a fourth ring portion received within the second end portion of the support member, wherein the first support frame and the second support frame are flexible or semi-rigid, wherein the first contacting member and the second contacting member are each configured and arranged to contact the user over a limited contacting region, and wherein the limited contacting region corresponds to an area over a maxilla at a canine fossa region, which includes a valley at a base of a zygomatic bone but does not overlie the zygomatic bones.

8. The patient interface device of claim 7, wherein the sealing assembly comprises a pair of prongs, a cushion, or a cushion and a faceplate.

9. The patient interface device of claim 7, further comprising an angled conduit member having a first end received within the third ring member of the first headgear support and a second end adapted to be coupled to a source of the flow of gas.

10. The patient interface device of claim 7, further comprising
a headgear assembly operatively coupled to the first headgear support and the second headgear support.

11. The patient interface device of claim 7, wherein the sealing assembly is rotatable relative to the first contacting member and the second contacting member.

12. The patient interface device of claim 7, wherein the support member and the sealing assembly are coupled together to define a gas flow path.

* * * * *